(12) United States Patent
Taga et al.

(10) Patent No.: US 11,813,553 B2
(45) Date of Patent: Nov. 14, 2023

(54) THREE-PORT CHAMBER FOR PROCESSING PARTICLES

(71) Applicant: Terumo BCT, Inc., Lakewood, CO (US)

(72) Inventors: Timothy Michael Taga, Arvada, CO (US); Anne Baker Oram, Lakewood, CO (US); Linda A. Taylor, Littleton, CO (US); Dennis J. Hlavinka, Arvada, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

(21) Appl. No.: 17/870,916

(22) Filed: Jul. 22, 2022

(65) Prior Publication Data

US 2022/0355222 A1 Nov. 10, 2022

Related U.S. Application Data

(60) Continuation of application No. 16/991,254, filed on Aug. 12, 2020, now Pat. No. 11,446,589, which is a
(Continued)

(51) Int. Cl.
*B01D 21/26* (2006.01)
*B04B 5/04* (2006.01)
*C12M 1/00* (2006.01)

(52) U.S. Cl.
CPC .......... *B01D 21/262* (2013.01); *B04B 5/0442* (2013.01); B04B 2005/0471 (2013.01); C12M 47/04 (2013.01)

(58) Field of Classification Search
CPC ................ B01D 21/262; B04B 5/0442; B04B 2005/0471; B04B 1/16; B04B 7/00;
(Continued)

(56) References Cited

U.S. PATENT DOCUMENTS 2,616,619 A 11/1952 MacLeod
3,391,597 A 7/1968 Gropper
(Continued)

FOREIGN PATENT DOCUMENTS

DE 2658926 A1 6/1978
DE 2701976 A1 7/1978
(Continued)

OTHER PUBLICATIONS

Figdor et al, "Theory and Practice of Centrifugal Elutriation (CE), Factors Influencing the Separation of Human Blood Cells", Cell Biophysics 5, 1983, 105-118.
(Continued)

*Primary Examiner* — Walter D. Griffin
*Assistant Examiner* — Shuyi S. Liu
(74) *Attorney, Agent, or Firm* — Harness, Dickey & Pierce, P.L.C.

(57) ABSTRACT

Embodiments relate to systems, chambers, and methods for processing particles by washing, concentrating, and/or treating the particles. Some embodiments provide for the processing of cells that may be in a liquid medium (e.g., a liquid in which the cells were grown) and are processed by being washed and concentrated for later use in research or other therapies.

18 Claims, 17 Drawing Sheets

Related U.S. Application Data division of application No. 14/827,130, filed on Aug. 14, 2015, now Pat. No. 10,765,971.

(60) Provisional application No. 62/037,515, filed on Aug. 14, 2014.

(58) Field of Classification Search
CPC .......... B04B 11/00; C12M 47/04; C12N 5/00; A61M 1/00; B01L 3/00
USPC ........................................ 494/22, 23, 27, 29
See application file for complete search history.

(56) References Cited

U.S. PATENT DOCUMENTS

| | | | |
|---|---|---|---|
| 3,987,961 | A | 10/1976 | Sinn et al. |
| 4,187,979 | A | 2/1980 | Cullis et al. |
| 4,256,120 | A | 3/1981 | Finley |
| 4,443,345 | A | 4/1984 | Wells |
| 4,720,284 | A | 1/1988 | McCarty |
| 4,921,473 | A | 5/1990 | Lee et al. |
| 4,939,087 | A | 7/1990 | Van Wie |
| 4,990,132 | A | 2/1991 | Unger et al. |
| 5,039,401 | A | 8/1991 | Columbus et al. |
| 5,405,308 | A | 4/1995 | Headley et al. |
| 5,577,513 | A | 11/1996 | Van Vlasselaer |
| 5,674,173 | A | 10/1997 | Hlavinka et al. |
| 5,722,926 | A | 3/1998 | Hlavinka et al. |
| 5,792,372 | A | 8/1998 | Brown et al. |
| 5,858,251 | A | 1/1999 | Borchardt et al. |
| 5,906,570 | A | 5/1999 | Langley et al. |
| 5,913,768 | A | 6/1999 | Langley et al. |
| 5,939,319 | A | 8/1999 | Hlavinka et al. |
| 5,951,877 | A | 9/1999 | Langley et al. |
| 6,022,306 | A | 2/2000 | Dumont et al. |
| 6,051,146 | A | 4/2000 | Green et al. |
| 6,053,856 | A | 4/2000 | Hlavinka |
| 6,071,422 | A | 6/2000 | Hlavinka et al. |
| 6,334,842 | B1 | 1/2002 | Hlavinka et al. |
| 6,352,499 | B1 | 3/2002 | Geigle |
| 6,354,986 | B1 | 3/2002 | Hlavinka et al. |
| 6,514,189 | B1 | 2/2003 | Hlavinka et al. |
| 6,574,173 | B1 | 6/2003 | Manes |
| 6,616,019 | B2 | 9/2003 | D'Alessio et al. |
| 7,029,430 | B2 | 4/2006 | Hlavinka et al. |
| 7,201,848 | B2 | 4/2007 | Antwiler et al. |
| 7,549,956 | B2 | 6/2009 | Hlavinka et al. |
| 7,588,692 | B2 | 9/2009 | Antwiler et al. |
| 7,857,744 | B2 | 12/2010 | Angley et al. |
| 7,963,901 | B2 | 6/2011 | Angley et al. |
| 8,066,888 | B2 | 11/2011 | Sweat et al. |
| 8,226,537 | B2 | 7/2012 | Pittinger et al. |
| 8,992,402 | B2 | 3/2015 | Holmes |
| 2003/0116512 | A1 | 6/2003 | Antwiler et al. |
| 2005/0051466 | A1 | 3/2005 | Carter et al. |
| 2006/0086675 | A1 | 4/2006 | Purdum |
| 2006/0147895 | A1 | 7/2006 | Purdum |
| 2007/0102374 | A1 | 5/2007 | Kolenbrander |
| 2008/0318756 | A1 | 12/2008 | Angley et al. |
| 2012/0316049 | A1 | 12/2012 | Holmes |
| 2012/0316051 | A1* | 12/2012 | Holmes ................. B04B 5/0442 494/42 |
| 2013/0045852 | A1* | 2/2013 | Chapman ............... B01D 21/26 494/36 |
| 2013/0203582 | A1* | 8/2013 | Katz ................... A61M 1/3696 494/37 |
| 2016/0030486 | A1* | 2/2016 | Cimino ................. C12M 27/02 435/378 |
| 2020/0368645 | A1 | 11/2020 | Taga et al. |

FOREIGN PATENT DOCUMENTS

| | | |
|---|---|---|
| DE | 3700122 A1 | 7/1988 |
| DE | 3734170 A1 | 4/1989 |
| EP | 0406485 A1 | 1/1991 |
| EP | 0408462 A2 | 1/1991 |
| WO | 8706857 A1 | 11/1987 |
| WO | 9633203 A1 | 10/1996 |
| WO | 9818403 A1 | 5/1998 |
| WO | 2008051847 A2 | 5/2008 |
| WO | 2012173754 A1 | 12/2012 |
| WO | 2012174007 A1 | 12/2012 |

OTHER PUBLICATIONS

Grabske, Robert, "Separating Cell Populations by Elutriation", Beckman Instruments, 1978, pp. 1-8.

International Search Report and Written Opinion, PCT/US2015/045409, dated Nov. 26, 2015.

Lutz et al, "Large-Scale Cell Separation by Centrifugal Elutriation", Analytical Biochemistry, 1992, 200:376-380.

Sanderson et al, "Design Principles for a Counterflow Centrifugation Cell Separation Chamber", Analytical Biochemistry, 1976, 71:615-622.

Tulp et al, "A Separation Chamber to Sort Cells and Cell Organelles by Weak Physical Forces. V.A. Sector-Shaped Chamber and Its Application to the Separation of Peripheral Blood Cells", J. of Immunological Methods, 1984, 69:281-295.

Communication pursuant to Article 94(3) EPC, EP Patent Application No. 15763442.9, dated Aug. 2, 2018.

Office Action, Canadian Patent Application No. 2957407, dated Apr. 30, 2019.

Official Action, Russian Patent Application No. 2017107980, dated Feb. 5, 2019 [English language translation included].

Notice of Reasons for Refusal, Japanese Patent Application No. 12017-507969, dated May 7, 2019 (English language translation included).

Communication pursuant to Article 94(3) EPC, EP Patent Application No. 15763442.9, dated Jul. 1, 2019.

Official Action for U.S. Appl. No. 16/991,261, dated Nov. 2, 2021 (9 Pages).

* cited by examiner

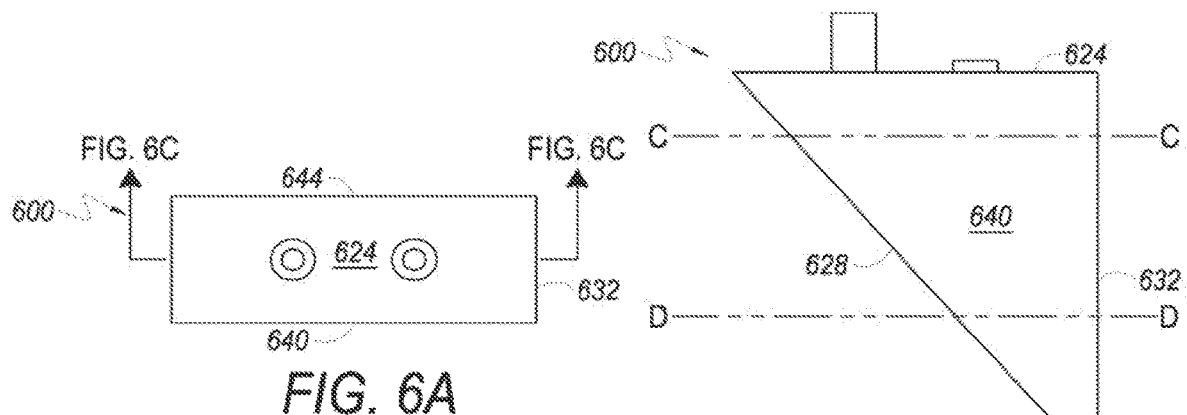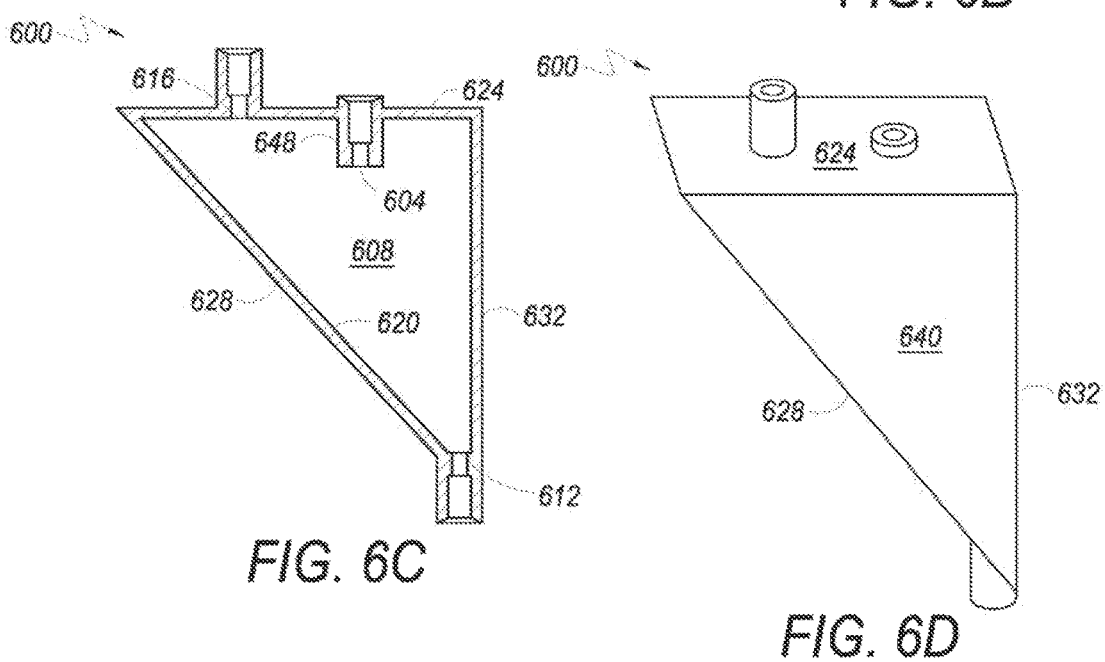
FIG. 6A  FIG. 6B  FIG. 6C  FIG. 6D

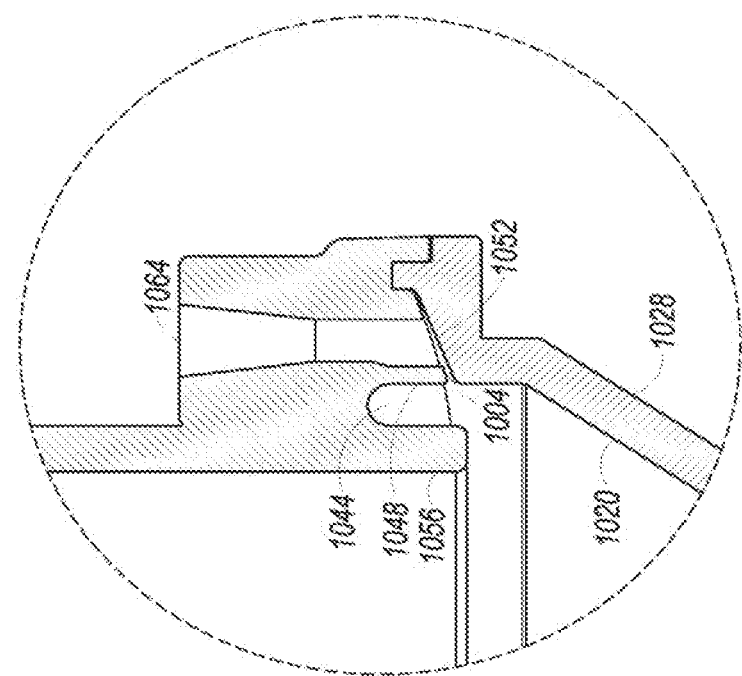
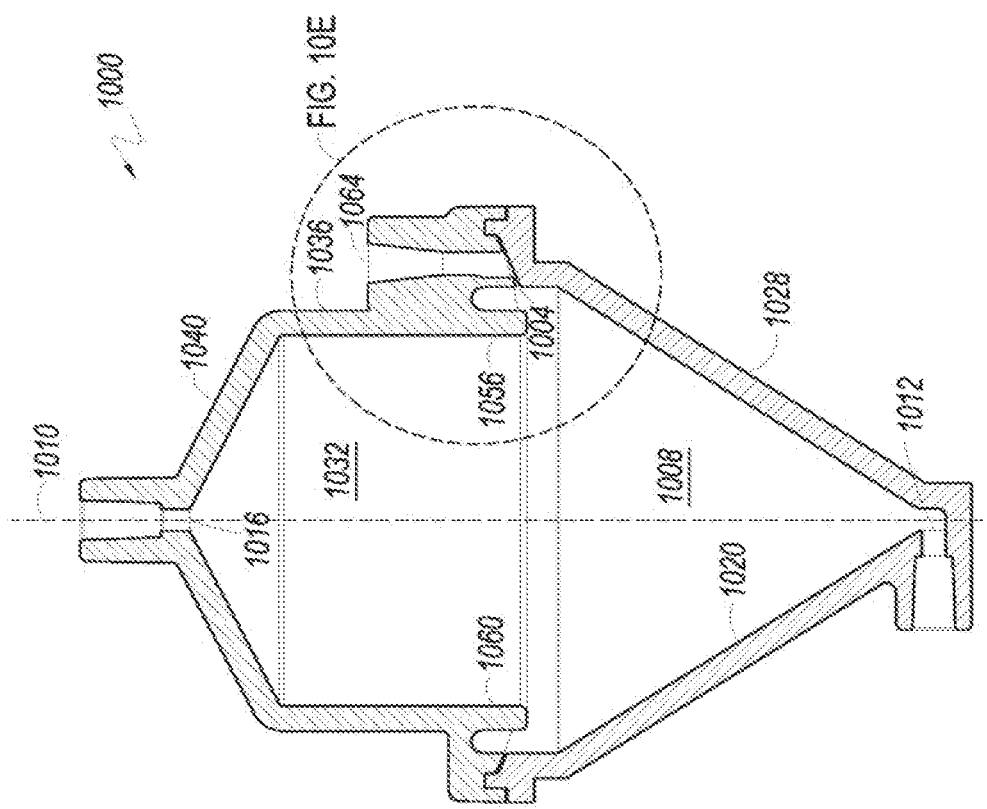

THREE-PORT CHAMBER FOR PROCESSING PARTICLES

CROSS-REFERENCE TO RELATED APPLICATIONS

This application is a continuation application of and claims priority to, U.S. patent application Ser. No. 16/991,254 filed on Aug. 12, 2020, which is a divisional application of U.S. patent application Ser. No. 14/827,130 filed on Aug. 14, 2015, now U.S. Pat. No. 10,765,971 issued on Sep. 8, 2020, which claims priority to U.S. Provisional Patent Application No. 62/037,515, filed Aug. 14, 2014. All of the above applications are hereby incorporated by reference herein in their entireties.

BACKGROUND

Several processes require the concentration of particles. Particles may be suspended or carried in a first volume of liquid and for additional processing, it may be useful to concentrate the particles into a second volume that is less than the first volume. For example, within the biological sciences there exists a need for concentrating cells. One example where this is necessary is during an apheresis procedure where cellular components of blood, e.g., leukocytes, erythrocytes, thrombocytes, are separated/concentrated from other liquid components such as plasma. Another example is the post processing of cells that may be grown in a liquid medium for therapeutic or research purposes. The cells may be separated/concentrated with respect to the liquid medium in which they are grown. The separation or concentration of the cells must occur without having a significant effect on their viability for later use.

Embodiments of the present invention have been made in light of these and other considerations. However, the relatively specific problems discussed above do not limit the applicability of the embodiments of the present invention.

SUMMARY

The summary is provided to introduce aspects of some embodiments of the present invention in a simplified form, and is not intended to identify key or essential elements of the claimed invention, nor is it intended to limit the scope of the claims.

Embodiments relate to apparatuses, systems, and methods for processing particles by washing, concentrating, and or treating the particles. Some embodiments provide for a chamber that includes an entry port for introducing a first liquid and particles into a volume of the chamber. The chamber also includes a first exit port, located below the entry port, for removing the particles from the volume of the chamber after the particles have been processed. In some embodiments, a liquid may be introduced into the chamber volume through the first exit port in order to perform some processing steps, e.g., washing of the particles. A second exit port of the chamber is located above the first exit port and is utilized for removing liquid from the volume of the chamber. The chamber also includes a sloped surface that directs at least a portion of the particles, introduced into the volume, toward the first exit port.

Other embodiments relate to method of processing particles. The methods may include use of a chamber and provide for subjecting the chamber to a centrifugal field by rotating the chamber. A first volume of particles and liquid may be introduced into a chamber volume through a first port. A second liquid may be introduced into the chamber volume through a second port. In embodiments, the second port may be positioned in a higher force region of the centrifugal field than the first port. Liquid may be removed through a third port, which may be positioned in a lower force region of the centrifugal field than the first port to concentrate cells in the chamber volume. After concentration, a second volume of particles and liquid may be removed through the second port. The second volume may include a concentrated amount of particles compared to the first volume.

BRIEF DESCRIPTION OF THE DRAWINGS

Non-limiting and non-exhaustive embodiments are described with reference to the following figures.

FIGS. 6A-D illustrate a chamber consistent with a second embodiment.

FIGS. 10A-E illustrate views of a chamber consistent with a sixth embodiment.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Embodiments below may be described with respect to processing cells such as by separating cells from other cells or liquid components, concentrating cells, and/or washing cells. However, this is done simply for illustrative purposes. It is noted that the embodiments are not limited to the description below. The embodiments are intended for use in products, processes, devices, and systems that process organic or inorganic particles, particulates, agglomerates. Accordingly, embodiments are not limited to separation, concentration, or washing of cells, e.g., cellular components in whole blood, but may be used to separate any particle from any liquid.

Figure 1:
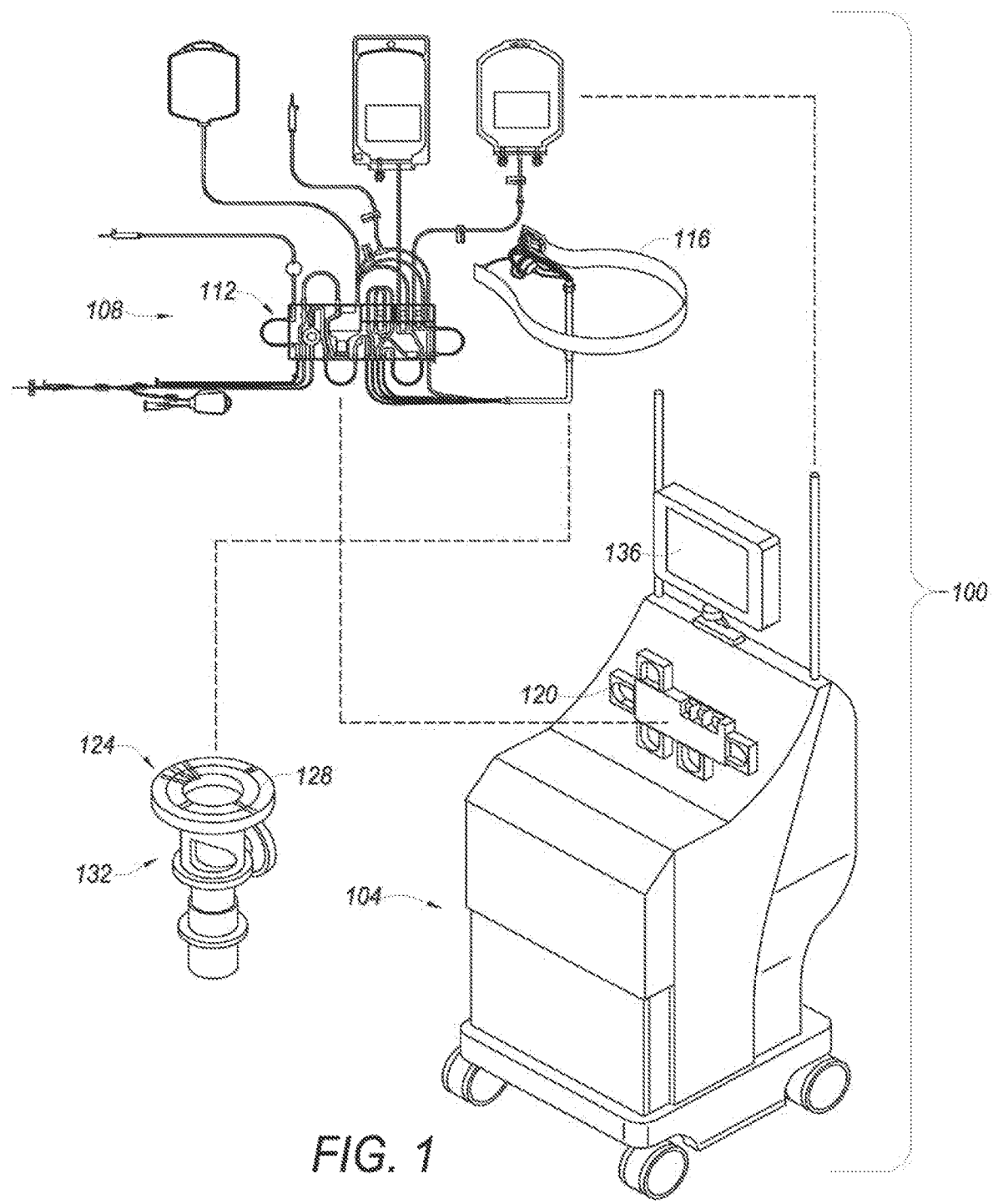
FIG. 1 illustrates an embodiment of a separation system, which can be used in, or with, embodiments.

FIG. 1 illustrates one embodiment of a separation system 100, which can be used in, or with, embodiments. In some embodiments, separation system 100 provides for a continuous whole blood separation process. In other embodiments, separation system 100 provides for concentrating and washing cells. In one embodiment, whole blood is withdrawn from a donor and is substantially, continuously provided to a separation device 104 where the blood is separated into various components and at least one of these components is collected from the device 104. One or more of the separated components may be either collected for subsequent use or returned to the donor. In embodiments, blood is withdrawn from the donor and directed through a bag and tubing set 108, which includes a tubing circuit 112, and a liquid processing vessel 116, which together define a closed, sterile and disposable system. The set 108 is adapted to be mounted in the separation device 104. The separation device 104 includes a pump/valve/sensor assembly 120, which interfaces with the tubing circuit 112, and a centrifuge assembly 124, which interfaces with the liquid processing vessel 116.

In another embodiment, a volume of cells in liquid (e.g., suspended or carried in liquid) is withdrawn from a storage container and is substantially, continuously provided to separation device 104 where the cells are collected from the device 104 after concentrating and/or washing. Additional liquid from processing the volume of cells in liquid may be discarded. In embodiments, a bag with the volume of cells and liquid may be directed through tubing set 108, which includes a tubing circuit 112, and a liquid processing vessel 116, which together define a closed, sterile and disposable system. The set 108 is adapted to be mounted in the separation device 104, as noted above.

Examples of separation systems that may be the basis of systems used with embodiments of the present invention, e.g., separation system 100, include the SPECTRA OPTIA® apheresis system, COBE® spectra apheresis system, and the TRIMA ACCEL® automated blood collection system, all manufactured by Terumo BCT, Inc. of Lakewood, Colo.

The centrifuge assembly 124 may include a channel 128 in a rotatable rotor assembly 128 (e.g., centrifuge), where the channel 128 may be used to hold a liquid processing vessel, e.g., vessel 116. The rotor assembly 132 may rotate to create a centrifugal field. The rotor assembly 132 may be configured to hold a chamber used to separate, concentrate, and/or wash cells. In one example, when whole blood is processed, cellular components of blood may be separated from each other and from liquid components of blood. In other examples, a volume of liquid containing cells may be processed with centrifuge assembly 124 to concentrate the volume of cells.

The liquid processing vessel 116 may be fitted within the channel 128. In one example, blood can flow substantially continuously from a donor, through the tubing circuit 112, and into the rotating liquid processing vessel 116. Within the liquid processing vessel 116, blood may be separated into various blood component types and at least one of these blood component types (e.g., white blood cells, platelets, plasma, or red blood cells) may be removed from the liquid processing vessel 116 and further processed. Blood components that are not being retained for collection or for therapeutic treatment (e.g., platelets and/or plasma) may also be removed from the liquid processing vessel 116 and returned to the donor via the tubing circuit 112.

In another example, a relatively large volume of liquid containing particles (e.g., cells) may be preprocessed using the liquid processing vessel 116. The volume of liquid and cells may be initially flowed into the liquid processing vessel 116 from tubing circuit 112. Within the liquid processing vessel 116, at least a portion of the liquid may be separated from the particles and removed from the liquid processing vessel 116 through tubing circuit 112. A portion of the cells and liquid may be retained for further processing.

Various alternative systems (not shown) may also be used with embodiments of the present invention, including batch processing systems or smaller scale batch or continuous separation systems.

Operation of the separation device 104 may be controlled by one or more processors included therein, and may comprise a plurality of embedded computer processors that are part of a computer system. The computer system may also include components that allow a user to interface with the computer system, including for example, memory and storage devices (RAM, ROM (e.g., CD-ROM, DVD), magnetic drives, optical drives, flash memory); communication/networking devices (e.g., wired such as modems/network cards, or wireless such as Wi-Fi); input devices such keyboard(s), touch screen(s), camera(s), and/or microphone(s); and output device(s) such as display(s), and audio system(s). In order to interface with an operator of the system 100, embodiments of the separation device 104 may include a graphical user interface 136 (shown in FIG. 1) with a display that includes an interactive touch screen.

Figure 2:
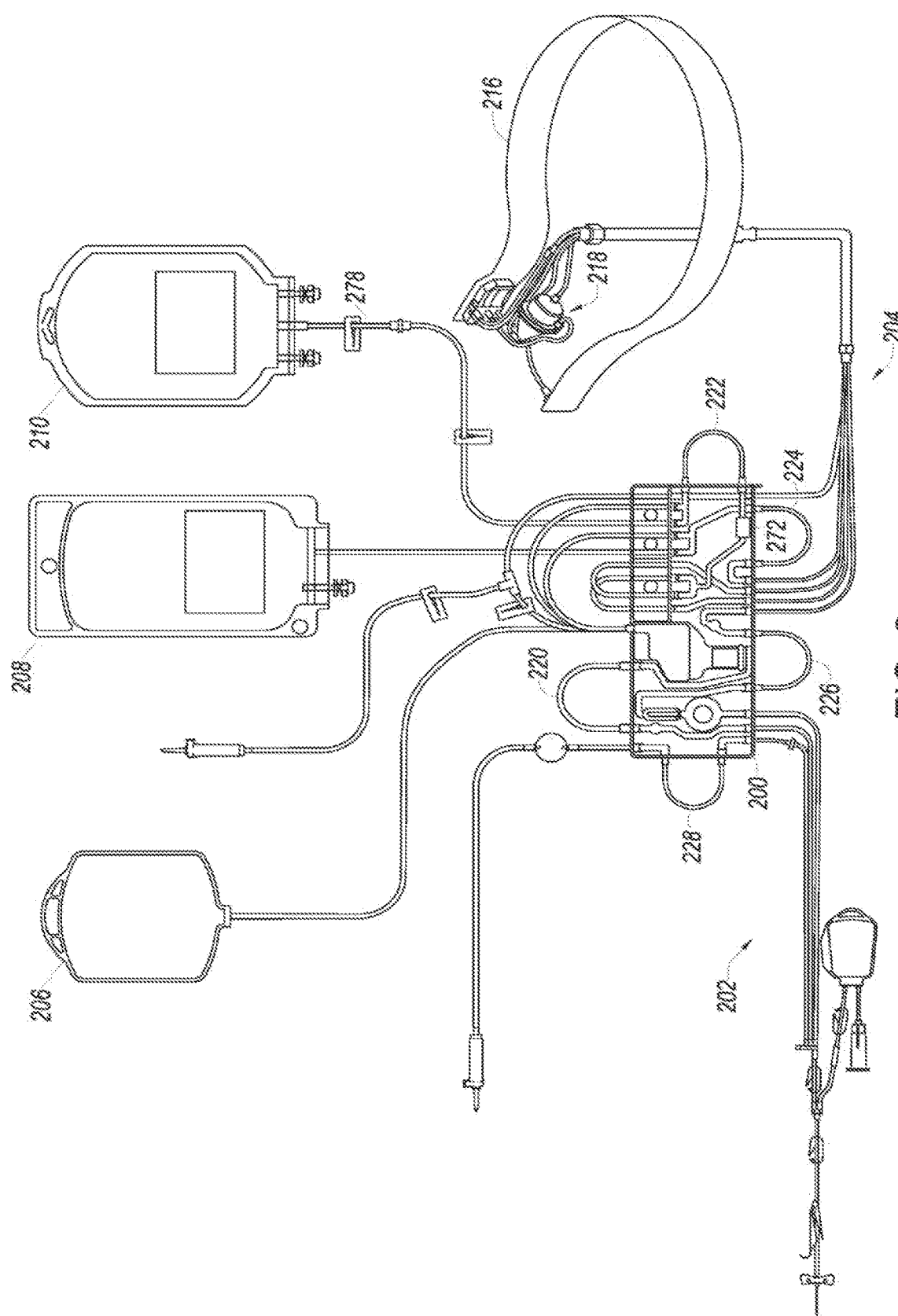
FIG. 2 illustrates a tubing and bag set for use in, or with, embodiments of the present invention.

An embodiment of a tubing circuit that may be used with embodiments is shown in FIG. 2, and as shown may include a cassette 200 and a number of tubing/storage assemblies 202, 204, 206, 208, and 210. In addition, tubing loops 220, 222, 224, 226, and 228 may engage with peristaltic pumps on a separation device, e.g., device 104, to pump fluids through the tubing/storage assemblies. The tubing circuit also includes chamber 218.

In embodiments, the tubing circuit shown in FIG. 2 may be used to separate whole blood into components. In embodiments, some components separated from whole blood may be returned to a donor, stored in one or more storage containers, or further processed. For example, whole blood may be circulated through tubing of the tubing circuit and into the liquid processing vessel 216, which is mounted on a rotor assembly (e.g., assembly 128). Chamber 218 may also be mounted on the rotor assembly.

In the liquid processing vessel 216, the blood may separate into components. Some components may be returned to a donor while others may be further processed. For example, chamber 218 may be used to further process (concentrate or wash components of whole blood). In one embodiment, red blood cells separated from whole blood may be introduced into chamber 218 and concentrated before being stored in a container, e.g., a bag. In other embodiments, the red blood cells may be washed or treated inside chamber 218, in addition to being concentrated, before being stored in a container. As another example, platelets may be directed to chamber 218 where they may be further processed (concentrated, washed, treated, etc.) before being stored in a container. Examples of chambers that may be used as chamber 218 in some embodiments are described in greater detail below, including description of some chamber designs that have entry ports and exit ports in specific locations (FIGS. 5A-11E).

Figure 3:
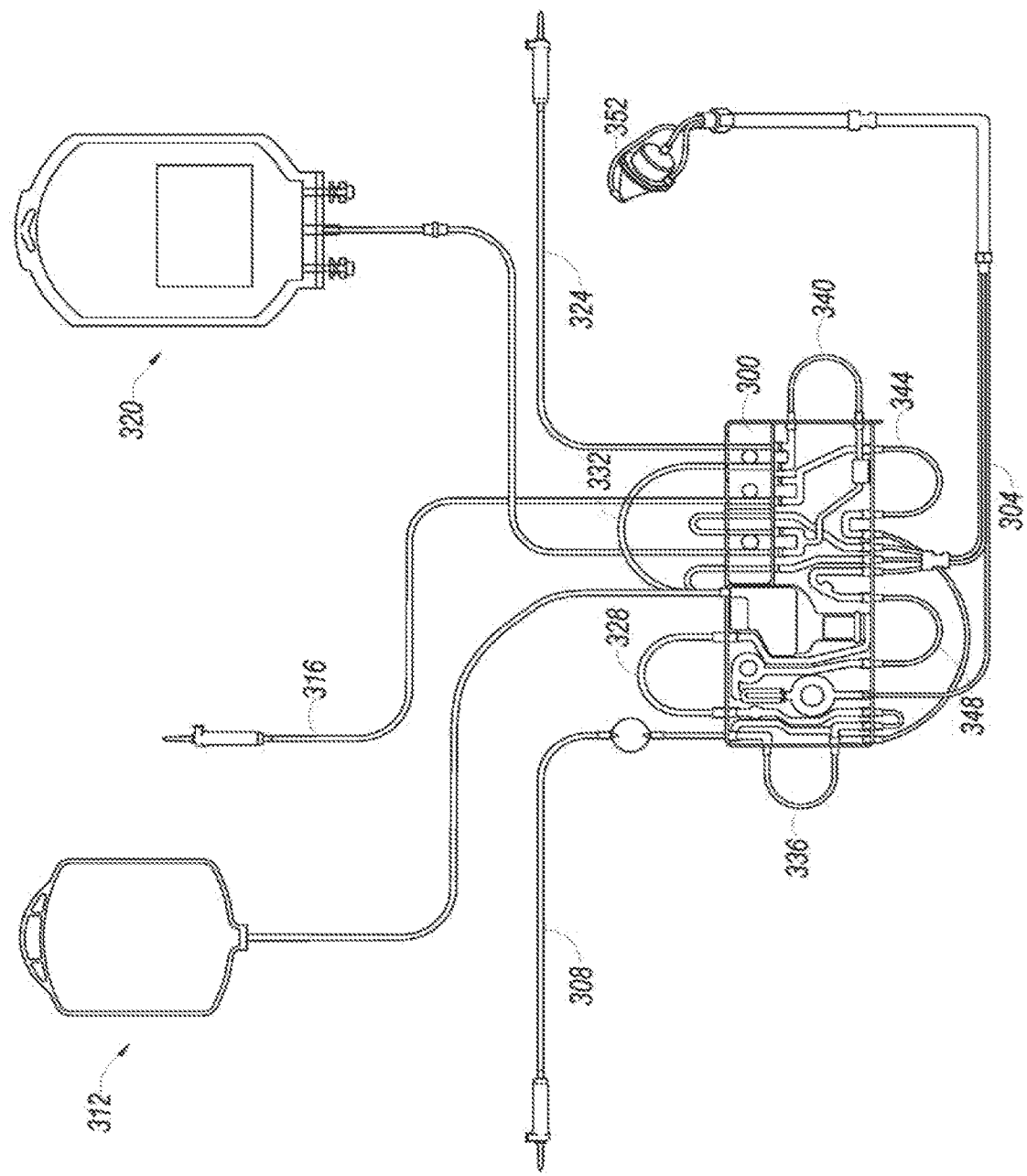
FIG. 3 illustrates another example of a tubing and bag set for use in, or with, embodiments.

Another embodiment of a tubing circuit that may be used with embodiments is shown in FIG. 3. The tubing circuit includes a cassette 300 and a number of tubing/storage assemblies 304, 308, 312, 316, 320, and 324. In addition, tubing loops 328, 332, 336, 340, 344, and 348 may engage with peristaltic pumps to pump fluids through cassette 300 and the tubing/storage assemblies. Assembly 312 provides a vent container, e.g., bag that allows air displaced by liquid flowing in the tubing circuit to be discharged into the vent container. The tubing circuit also includes a chamber 352. Examples of chambers that may be used as chamber 352 in some embodiments are described in greater detail below (FIGS. 5A-11E).

In embodiments, the tubing circuit shown in FIG. 3 may be used to concentrate a volume of particles, e.g., cells, in liquid. In embodiments, the tubing circuit may be mounted on a separation device so that chamber 352 is mounted on a rotor assembly (e.g., assembly 128 with a centrifuge), which rotates the chamber 352.

Initially, a container storing the volume of particles with liquid may be attached to tubing assembly 316. The particles in liquid may flow through tubing in the tubing circuit and into chamber 352. As described in greater detail below, some embodiments provide for specific chamber designs that have entry ports and exit ports in specific locations. As the chamber 352 rotates, it may separate some liquid from the particles and the removed liquid may flow through tubing into a container, e.g., a waste bag in assembly 320.

In some embodiments, the particles, in addition to being concentrated, may be washed or treated. In these embodiments, a wash or treatment liquid storage container may be attached to tubing assembly 308. The wash or treating liquid may flow through tubing into chamber 352 to wash or treat the particles after, or during, concentration. The used wash or treatment fluid may flow out of chamber 352 and into waste bag assembly 320.

After the particles have been processed (concentrated, washed, and/or treated), they may flow from chamber 352 through tubing in the tubing circuit and through tubing assembly 324. In some embodiments, a storage container may be attached to tubing assembly 324 to store the processed particles. In other embodiments, tubing assembly 324 may be attached to an inlet of other tubing sets that are used to further process the particles.

Figure 4:
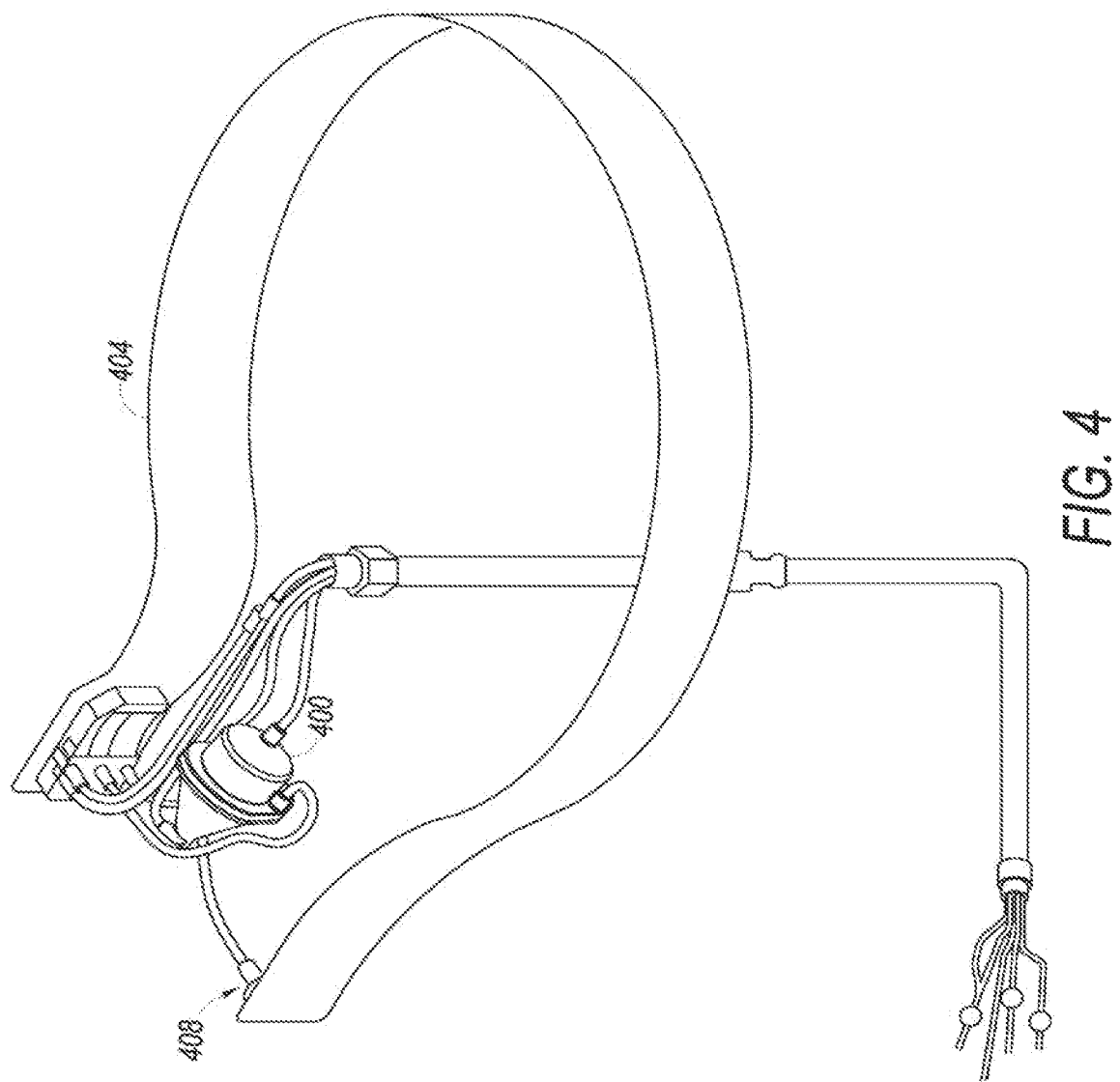
FIG. 4 illustrates a liquid processing vessel and an embodiment of a chamber that may be used in combination in some embodiments.

In some embodiments, the tubing circuit shown in FIG. 3 may include some additional components. For example, shown in FIG. 4 is a chamber 400 (which may be similar to chamber 352), connected to a liquid processing vessel 404 (which may be similar to vessel 216). In some embodiments, the liquid processing vessel 404 may be used for preprocessing of a volume of particles in liquid prior to processing in chamber 400.

As one example, if the volume of liquid with particles is relatively large, or it is desirable to process the volume at a high flow rate, it may not be possible to process the volume directly by chamber 400. In these embodiments, vessel 404 may be used in a pre-processing step that allows larger volumes (or flow rates) of liquid to be processed. For example, a centrifuge assembly (e.g., assembly 124) may include a channel in a rotatable rotor assembly (e.g., centrifuge), where the channel may be used to hold the liquid processing vessel 404. The rotor assembly may rotate to create a centrifugal field. The rotor assembly may also be configured to hold chamber 400.

Liquid (with the particles) may flow into vessel 404 through port 408. As the liquid flows around the vessel 404, which is rotating, liquid with the particles may separate from other liquid that does not include the particles, creating a concentrated volume of particles and liquid. The separated liquid (without particles) may be directed to a waste bag, with the a more concentrated stream of liquid and particles flowing into chamber 400, where the particles may be further concentrated, washed, and/or treated.

FIGS. 2-4 illustrate some embodiments of tubing circuits with chambers and vessels that are consistent with embodiments of the present invention. In embodiments, the tubing circuits of FIGS. 2-4 can be disposable so that they are used one time to process a volume of liquid, e.g., blood, cells in growing medium, cells in storage medium etc., and then discarded. In other embodiments, the tubing circuits can be reposable (reused) or include one or more component(s) that are reposable.

It is noted that the present invention is not limited to the specific tubing circuit configurations shown in FIGS. 2-4 and described above. Other tubing assembly arrangements, including additional components not shown in FIGS. 2-4 may be utilized in embodiments. For example, in some embodiments a tubing circuit may combine features of FIG. 3 and FIG. 4 and include additional tubing that provides flow paths to the various components.

Below in FIGS. 5A-11E are various views of chamber designs that are consistent with embodiments of the present invention. It is noted that although specific examples are provided, the present invention is not necessarily limited to the features of any one of the embodiments. The embodiments shown in FIGS. 5A-11E are provided to illustrate some features and illustrate examples of some embodiments. The present invention is therefore not limited to any specific embodiment.

As described in greater detail below, any of the chambers 500, 600, 700, 800, 900, and 1000 shown in FIGS. 5A-11C may be used in embodiments to process particles. In some embodiments, the chambers may be used to concentrate, wash, and treat particles, such as cells. In other embodiments, the chambers may be used in an elutriation process, where particles of different sizes may be separated and collected separately from a mixture of liquid and multi-sized particles, e.g., cells.

Figure 5A:
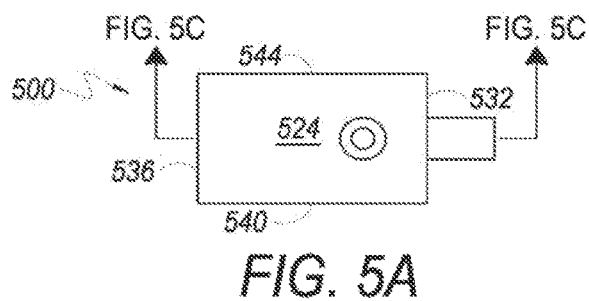
FIGS. 5A-D illustrate a chamber consistent with a first embodiment.
Figure 5B:
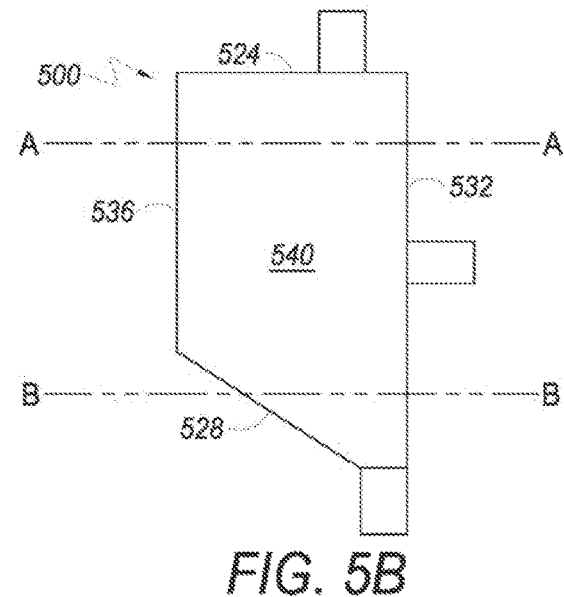
Figure 5C:
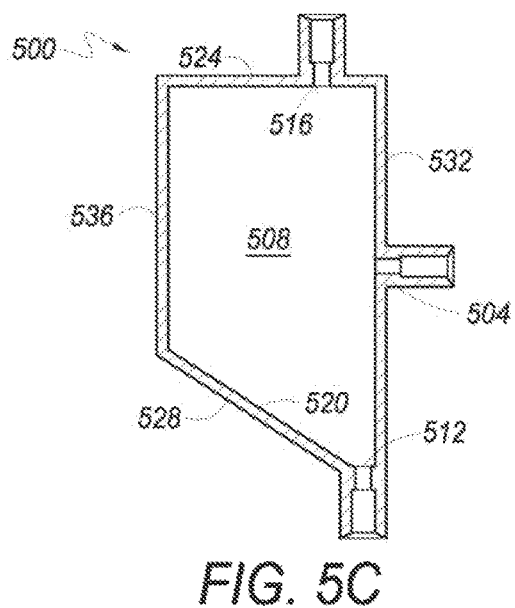
Figure 5D:
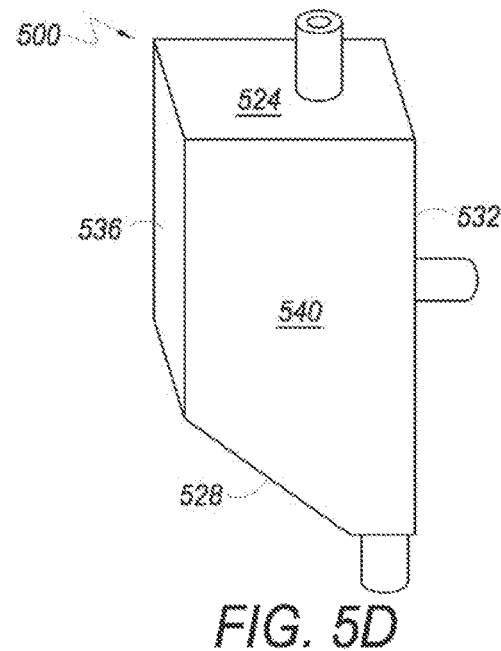

FIGS. 5A-D illustrate four views of a chamber that may be used in embodiments to concentrate, wash, and/or treat particles in a liquid, such as cells in a liquid medium. FIG. 5A illustrates a top plan view of chamber 500; FIG. 5B illustrates a side plan view of chamber 500; FIG. 5C illustrates a cross-sectional view of chamber 500; and FIG. 5D illustrates a perspective view of chamber 500.

Chamber 500 includes, inter alia, three ports. It is noted that by port, it is meant a perforation, e.g., a hole that allows liquid, particles, or other material to enter or exit a volume. Although reference numerals in the figures may point to different features of the chambers in the figures, it is noted that the ports are intended to refer to a perforation or hole in a wall or tube where liquid or particles enter or leave the volume of a chamber. The ports may be in fluid communication with pathways that direct liquid, particles, or other material through, or from, the port. In the figures, a reference numeral for a port may point to a pathway in fluid communication with the port, but the actual port is the perforation through which particles and/or liquid flow through as they enter or exit the chamber volume. The reference numeral may point to the pathway in order to avoid confusion by crowding items in the figures or if the port is not visible in the figure (e.g. FIGS. 12 and 14 below). However, where possible, the reference numerals point to the actual port.

As shown in FIG. 5C, chamber 500 includes port 504, which is an entry port that allows liquid and particles to be introduced into a volume 508 and may be located near a first cross section of volume 508 (e.g., cross section of chamber 500 through line AA in FIG. 5B). Port 512 is an exit port through which particles and some liquid are removed from volume 508 and may be located in a lower portion of volume 508. In addition, port 516 is an exit port through which liquid separated from the particles (in order to concentrate the particles in a smaller volume of liquid, wash the particles with the liquid, and/or treat the particles with the liquid) is removed. Port 516 may be located in a top portion of volume 508.

Chamber 500 also includes a sloped surface 520 that directs at least a portion of particles in volume 508 toward exit port 512. As illustrated in FIG. 5C, sloped surface 520 slopes toward exit port 512. In operation, chamber 500 may be subjected to a force, e.g., gravity or centrifugal force that generally moves particles toward exit port 512. Sloped surface 520 aids in directing particles toward exit port 512.

In addition to the features described above, chamber 500 also includes top wall 524, sloped wall 528, and four side walls 532, 536, 540, and 544. These walls define volume 508, which as shown is a trapezoidal volume with a rectangular cross section when sectioned along lines AA or BB (FIG. 5B).

One feature of chamber 500 is that it includes at least two cross-sectional areas (e.g., one taken at line AA and the other taken at line BB), where the first cross-sectional area is larger than the second cross-sectional area. As can be readily understood from FIGS. 5A and 5B the cross-sectional area taken along line AA would be rectangular and be of a larger area than a cross-sectional area taken along line BB. Without being bound by theory, it is believed that in some embodiments, this feature may provide a funneling effect toward exit port 512.

As shown in FIGS. 5A-D, exit port 516 is located in top wall 524. Although port 516 is shown in a particular location, in other embodiments, exit port 516 may be located along any portion of top wall 524. In other embodiments, exit port 516 may be in a side wall such as side walls 532, 536, 540, or 544. In some embodiments, the location of exit port 516 is not limited to any specific location, except that it is located above exit port 512.

Similarly, entry port 504 is in sidewall 532 and is shown in a particular location. However, in other embodiments, entry port 504 may be located in another location in side wall 532. In other embodiments, entry port 504 may be in a different side wall such as side walls 536, 540, or 544. In some embodiments, the location of entry port 504 is not limited to any specific location, except that it is located above exit port 512.

Sloped surface 520 is provided by sloped wall 528. Additionally, a portion of exit port 512 may be in sloped wall 528. However, in other embodiments, exit port 512 may be located in another location such as in side walls 532, 536, 540, or 544. In some embodiments, the location of exit port 512 is not limited to any specific location, except that it is located below entry port 504.

In some embodiments, processing of particles may provide for introducing liquid or other material through port 512. In these embodiments, port 512 may in addition to serving as an exit port for particles, may serve as an entry point for the liquid or other material.

FIGS. 6A-D illustrate four views of another chamber that may be used in embodiments to concentrate, wash, and/or treat particles in a liquid, such as cells in a liquid medium. FIG. 6A illustrates a top plan view of chamber 600; FIG. 6B illustrates a side plan view of chamber 600; FIG. 6C illustrates a cross-sectional view of chamber 600; and FIG. 6D illustrates a perspective view of chamber 600.

Chamber 600 includes, inter alia, three ports. As shown in FIG. 6C, chamber 600 includes port 604, which is an entry port that allows liquid and particles to be introduced into a volume 608 and may be located near a first cross section of volume 608 (e.g., cross section of chamber 600 through line CC in FIG. 6B). Port 612 is an exit port through which particles and some liquid are removed from volume 608 and may be located in a lower portion of volume 608. In addition, port 616 is an exit port through which liquid separated from the particles (in order to concentrate the particles in a smaller volume of liquid, wash the particles with the liquid, and/or treat the particles with the liquid) is removed. Port 616 may be located in a top portion of volume 608.

Chamber 600 also includes a sloped surface 620 that directs at least a portion of particles in volume 608 toward exit port 612. As illustrated in FIG. 6C, sloped surface 620 slopes toward exit port 612. In operation, chamber 600 may be subjected to a force, e.g., gravity or centrifugal force that generally moves particles toward exit port 612. Sloped surface 620 aids in directing particles toward exit port 612.

In addition to the features described above, chamber 600 also includes top wall 624, sloped wall 628, and three side walls 632, 640, and 644. These walls define volume 608, which as shown is a triangular volume, with a rectangular cross section when sectioned along lines CC or DD (FIG. 6B).

One feature of chamber 600 is that it includes at least two cross-sectional areas (e.g., one taken at line CC and the other taken at line DD), where the first cross-sectional area is larger than the second cross-sectional area. As can be readily understood from FIGS. 6A and 6B the cross-sectional area taken along line CC would be rectangular and be of a larger area than a cross-sectional area taken along line DD. Without being bound by theory, it is believed that in some embodiments, this feature may provide a funneling effect toward exit port 612.

As shown in FIGS. 6A-D, exit port 616 is located in top wall 624. Although port 616 is shown in a particular location, in other embodiments, exit port 616 may be located along any portion of top wall 624. In other embodiments, exit port 616 may be in a side wall such as walls 632, 640, and 644; or sloped wall 628. In some embodiments, the location of exit port 616 is not limited to any specific location, except that it is located above exit port 612.

Entry port 604 is located in down tube 648 and is shown in a particular location. However, in other embodiments, entry port 604 may be located in another location. For example, down tube 648 may be shorter or longer, which would change the location of entry port 604. In other embodiments, down tube 648 may extend from a different wall (not top wall 624), such as wall 628, 632, 640, or 644. In some embodiments, the location of entry port 604 is not limited to any specific location, except that it is located above exit port 612.

Sloped surface 620 is provided by sloped wall 628 and slopes toward exit port 612. Additionally, a portion of exit port 612 is in sloped wall 628. However, in other embodiments, exit port 612 may be located in another location such as in walls 632, 640, or 644. In some embodiments, the location of exit port 612 is not limited to any specific location, except that it is located below entry port 604.

In some embodiments, processing of particles may provide for introducing liquid or other material through port 612. In these embodiments, port 612 may in addition to serving as an exit port for particles, may serve as an entry point for the liquid or other material.

Figure 7A:
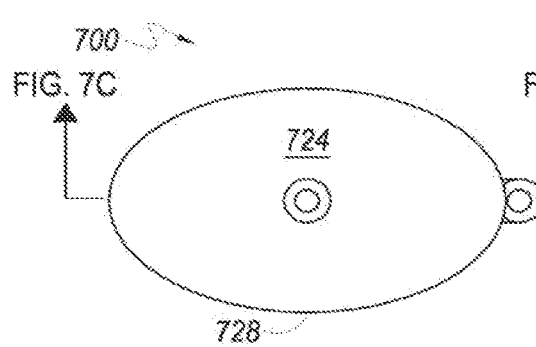
FIGS. 7A-D illustrate a chamber consistent with a third embodiment.
Figure 7B:
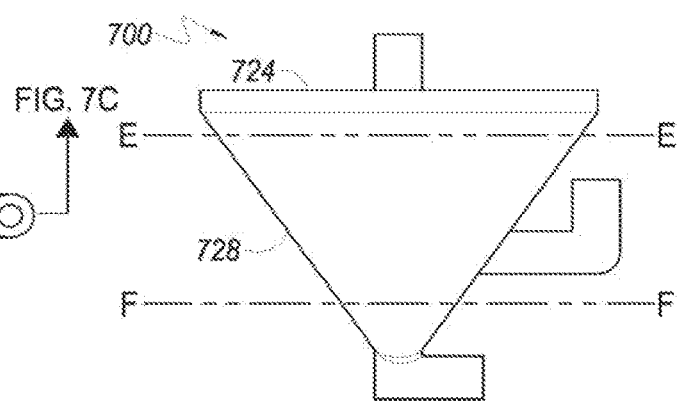
Figure 7C:
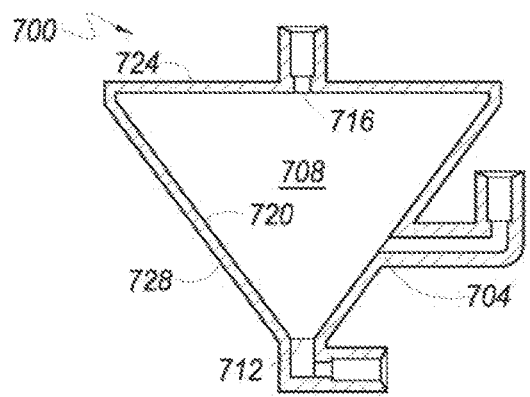
Figure 7D:
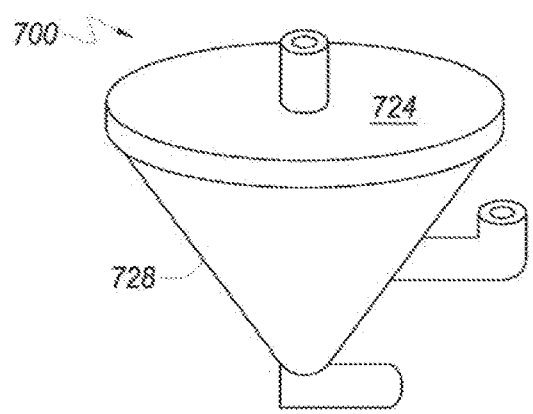

FIGS. 7A-D illustrate four views of another chamber that may be used in embodiments to concentrate, wash, and/or treat particles in a liquid, such as cells in a liquid medium. FIG. 7A illustrates a top plan view of chamber 700; FIG. 7B illustrates a side plan view of chamber 700; FIG. 7C illustrates a cross-sectional view of chamber 700; and FIG. 7D illustrates a perspective view of chamber 700.

Chamber 700 includes, inter alia, three ports. As shown in FIG. 7C, chamber 700 includes port 704, which is an entry port that allows liquid and particles to be introduced into a volume 708, and may be located near a first cross section of volume 708 (e.g., cross section of chamber 700 through line EE in FIG. 7B). Port 712 is an exit port through which particles and some liquid are removed from volume 708 and may be located in a lower portion of volume 708. In addition, port 716 is an exit port through which liquid separated from the particles (in order to concentrate the particles in a smaller volume of liquid, wash the particles with the liquid, and/or treat the particles with the liquid) is removed. Port 716 may be located in a top portion of volume 708.

Chamber 700 also includes a sloped surface 720 that directs at least a portion of particles in volume 708 toward exit port 712. As illustrated in FIG. 7C, sloped surface 720 slopes toward exit port 712. In operation, chamber 700 may be subjected to a force, e.g., gravity or centrifugal force that generally moves particles toward exit port 712. Sloped surface 720 aids in directing particles toward exit port 712.

In addition to the features described above, chamber 700 also includes top wall 724 and side wall 728. These walls define volume 708, which as shown is an elliptical, sloping volume, with an elliptical cross section perpendicular when sectioned along lines EE or FF (FIG. 7B).

One feature of chamber 700 is that it includes at least two cross-sectional areas (e.g., one taken at line EE and the other taken at line FF), where the first cross-sectional area is larger than the second cross-sectional area. As can be readily understood from FIGS. 7A and 7B, the cross-sectional area taken along line EE would be elliptical and be of a larger area than a cross-sectional area taken along line FF. Without being bound by theory, it is believed that in some embodiments, this feature may provide a funneling effect toward exit port 712.

As shown in FIGS. 7A-D, exit port 716 is located in top wall 724. Although port 716 is shown in a particular location, in other embodiments, exit port 716 may be located along any portion of top wall 724. In other embodiments, exit port 716 may be in side wall 728. In some embodiments, the location of exit port 716 is not limited to any specific location, except that it is located above exit port 712.

Entry port 704 is in sidewall 728 and is shown in a particular location. However, in other embodiments, entry port 704 may be located in another location in side wall 728. In other embodiments, entry port 704 may be in a down tube that may extend from side 728 or from top wall 724. In some embodiments, the location of entry port 704 is not limited to any specific location, except that it is located above exit port 712.

Sloped surface 720 is provided by side wall 728 and slopes toward exit port 712. Additionally, a portion of exit port 712 may be in side wall 728. However, in other embodiments, exit port 712 may be located in another location in side wall 728. In some embodiments, the location of exit port 712 is not limited to any specific location, except that it is located below entry port 704.

In some embodiments, processing of particles may provide for introducing liquid or other material through port 712. In these embodiments, port 712 may in addition to serving as an exit port for particles, may serve as an entry point for the liquid or other material.

Figure 8A:
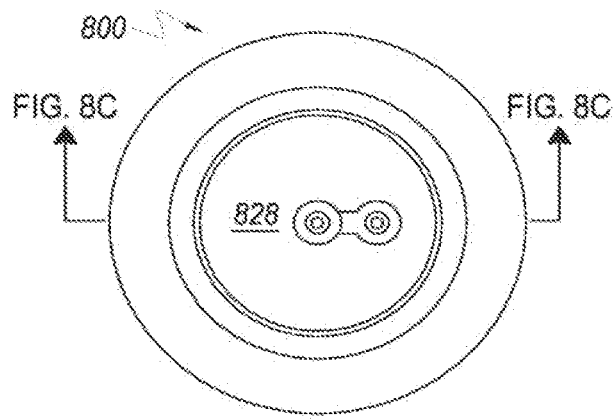
FIGS. 8A-D illustrate a chamber consistent with a fourth embodiment.
Figure 8B:
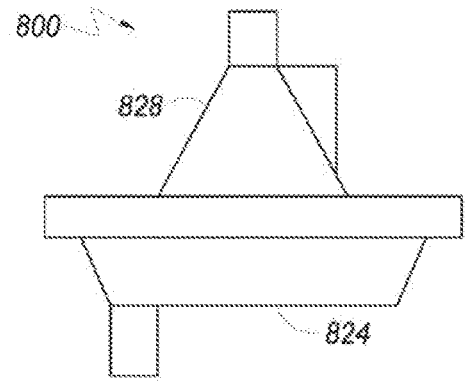
Figure 8C:
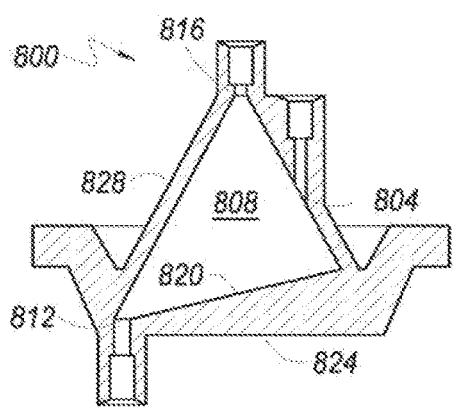
Figure 8D:
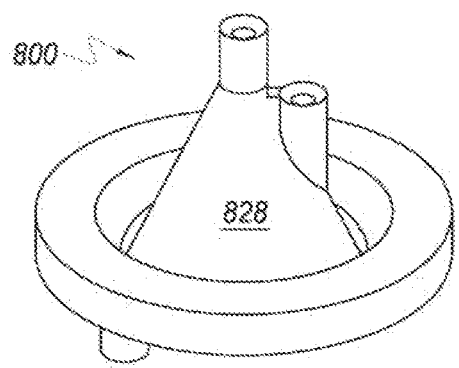

FIGS. 8A-D illustrate four views of another chamber that may be used in embodiments to concentrate, wash, and/or treat particles in a liquid, such as cells in a liquid medium. FIG. 8A illustrates a top plan view of chamber 800; FIG. 8B illustrates a side plan view of chamber 800; FIG. 8C illustrates a cross-sectional view of chamber 800; and FIG. 8D illustrates a perspective view of chamber 800.

Chamber 800 includes, inter alia, three ports. As shown in FIG. 8C, chamber 800 includes port 804, which is an entry port that allows liquid and particles to be introduced into a volume 808 and may be located in a center portion of volume 808. Port 812 is an exit port through which particles and some liquid are removed from volume 808 and may be located in a lower portion of volume 808. In addition, port 816 is an exit port through which liquid separated from the particles (in order to concentrate the particles in a smaller volume of liquid, wash the particles with the liquid, and/or treat the particles with the liquid) is removed. Port 816 may be located in a top portion of volume 808.

Chamber 800 also includes a sloped surface 820 that directs at least a portion of particles in volume 808 toward exit port 812. As illustrated in FIG. 8C, sloped surface 820 slopes toward exit port 812. In operation, chamber 800 may be subjected to a force, e.g., gravity or centrifugal force that generally moves particles toward exit port 812. Sloped surface 820 aids in directing particles toward exit port 812.

In addition to the features described above, chamber 800 also includes bottom wall 824 and side wall 828. These walls define volume 808, which as shown is a conical volume.

As shown in FIGS. 8A-D, exit port 816 is located at least partially in side wall 828. Although port 816 is shown in a particular location, in other embodiments, exit port 816 may be located along any portion of side wall 828. In some embodiments, the location of exit port 816 is not limited to any specific location, except that it is located above exit port 812.

Entry port 804 is in sidewall 828 and is shown in a particular location. However, in other embodiments, entry port 804 may be located in another location in side wall 828. In other embodiments, entry port 804 may be in a down tube that may extend from side wall 828 or from bottom wall 824. In some embodiments, the location of entry port 804 is not limited to any specific location, except that it is located above port 812.

Sloped surface 820 is provided by side wall 828 and slopes toward exit port 812. In embodiments, exit port 812 may be located in another location, such as in side wall 828. In some embodiments, the location of exit port 812 is not limited to any specific location, except that it is located below entry port 804.

In some embodiments, processing of particles may provide for introducing liquid or other material through port 812. In these embodiments, port 812 may in addition to serving as an exit port for particles, may serve as an entry point for the liquid or other material.

Figure 9A:
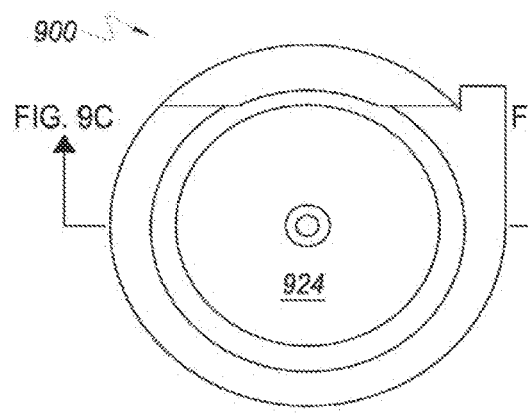
FIGS. 9A-D illustrate a chamber consistent with a fifth embodiment.
Figure 9B:
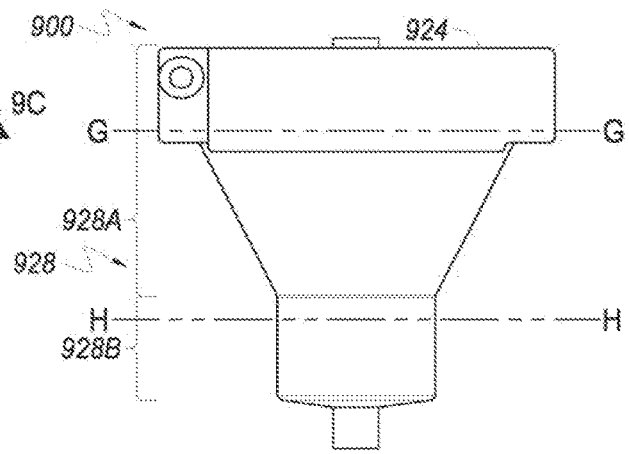
Figure 9C:
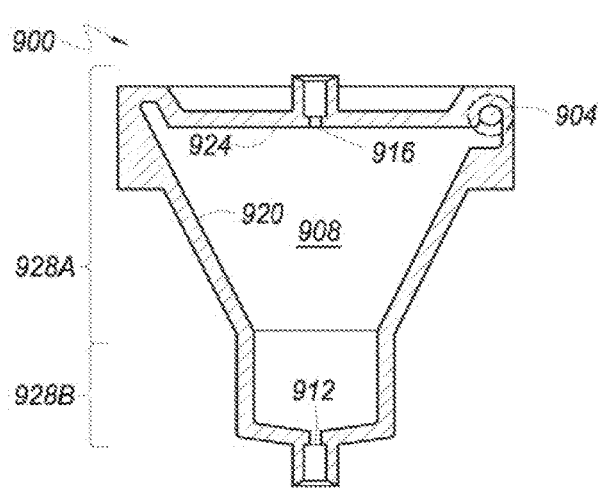
Figure 9D:
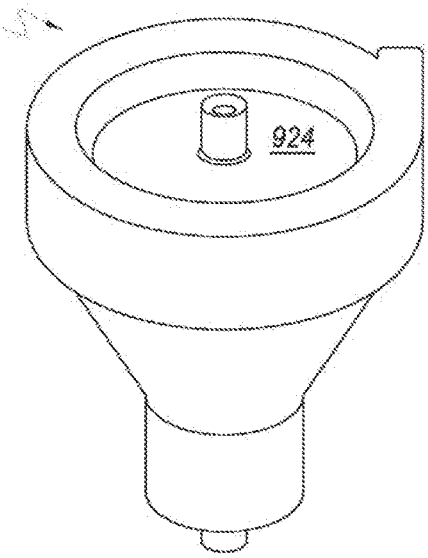

FIGS. 9A-D illustrate four views of yet another chamber that may be used in embodiments to concentrate, wash, and/or treat particles in a liquid, such as cells in a liquid medium. FIG. 9A illustrates a top plan view of chamber 900; FIG. 9B illustrates a side plan view of chamber 900; FIG. 9C illustrates a cross-sectional view of chamber 900, and FIG. 9D illustrates a perspective view of chamber 900.

Chamber 900 includes, inter alia, three ports. As shown in FIG. 9C, chamber 900 includes port 904, which is an entry port that allows liquid and particles to be introduced into a volume 908 and may be located near a first cross section of volume 908 (e.g., cross section of chamber 900 through line GG in FIG. 9B). Port 912 is an exit port through which particles and some liquid are removed from volume 908 and may be located in a lower portion of volume 908. Port 912 may in embodiments also be used as an entry port to introduce a liquid into the volume 908, such as to wash particles in volume 908. In addition, port 916 is an exit port through which liquid separated from the particles (in order to concentrate the particles in a smaller volume of liquid, wash the particles with the liquid, and/or treat the particles with the liquid) is removed. Port 916 may be located in a top portion of volume 908.

Chamber 900 also includes a sloped surface 920 that directs at least a portion of particles in volume 908 toward exit port 912. As illustrated in FIG. 9C, sloped surface 920 slopes toward exit port 912. In operation, chamber 900 may be subjected to a force, e.g., gravity or centrifugal force that generally moves particles toward exit port 912. Sloped surface 920 aids in directing particles toward exit port 912.

In addition to the features described above, chamber 900 also includes top wall 924 and side wall 928. These walls define volume 908, which as shown is a frusto-conical volume. As is shown, side wall 928 includes a first portion 928A and a second portion 928B.

One feature of chamber 900 is that it includes at least two cross-sectional areas (one taken at line GG and the other taken at line HH), where the first cross-sectional area is larger than the second cross-sectional area. As can be readily understood from FIGS. 9A and 9B, the cross-sectional area taken along line GG would be circular and be of a larger area than a cross-sectional area taken along line HH. Without being bound by theory, it is believed that in some embodiments, this feature may provide a funneling effect toward exit port 912.

As shown in FIGS. 9A-D, exit port 916 is located in top wall 924. Although port 916 is shown in a particular location, in other embodiments, exit port 916 may be located along any portion of top wall 924. In other embodiments, exit port 916 may be in side wall 928. In some embodiments, the location of exit port 916 is not limited to any specific location, except that it is located above exit port 912.

Entry port 904 is in sidewall 928 and is shown in a particular location. However, in other embodiments, entry port 904 may be located in another location in side wall 928. In other embodiments, entry port 904 may be in a down tube that may extend from top wall 924 or from side wall 928. In some embodiments, the location of entry port 904 is not limited to any specific location, except that it is located above exit port 912. Indeed, as illustrated in FIG. 9C, entry port 904 is located slightly above exit port 916.

Sloped surface 920 is provided by first portion of side wall 928A and slopes toward exit port 912. In other embodiments, exit port 912 may be located in another location, such as in a portion of side wall 928. In some embodiments, the location of exit port 912 is not limited to any specific location, except that it is located below entry port 904.

As noted above, processing of particles may provide for introducing liquid or other material through port 912. In these embodiments, port 912 may in addition to serving as an exit port for particles, may serve as an entry point for the liquid or other material.

FIGS. 10A-11E illustrate a chamber 1000 that may be used in other embodiments for processing particles, e.g., concentrate, wash, and/or treat particles in a liquid, such as cells in a liquid medium. As described in greater detail below, chamber 1000 includes some features that are similar to features of chambers 500, 600, 700, 800, and 900 described above. Chamber 1000 also includes some additional features that may be useful for processing some particles.

Figure 10A:
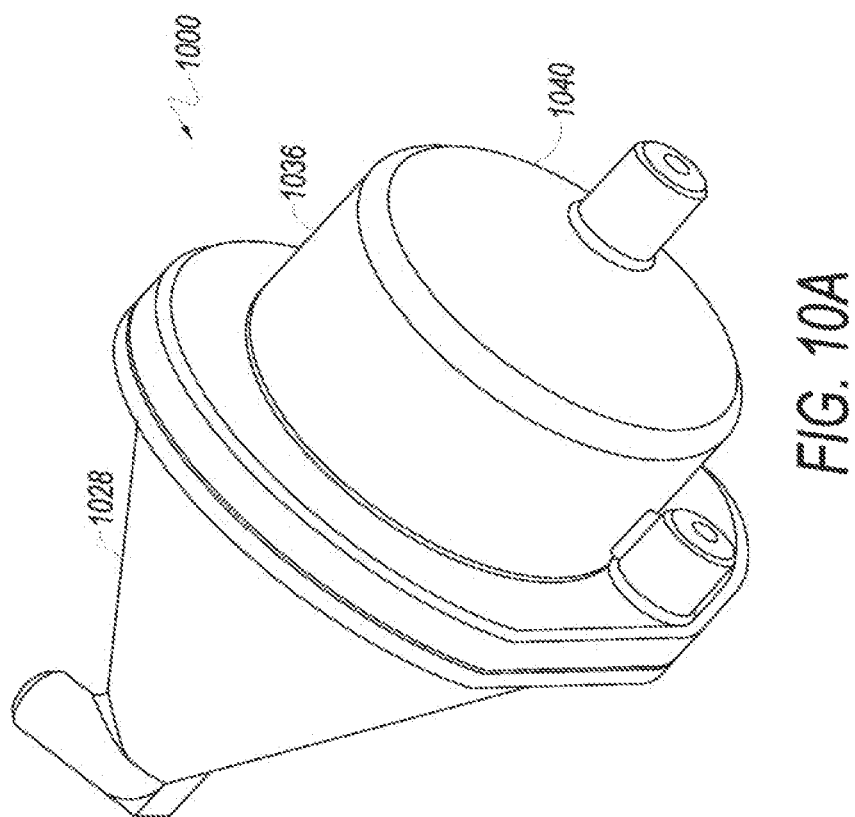
Figure 10C:
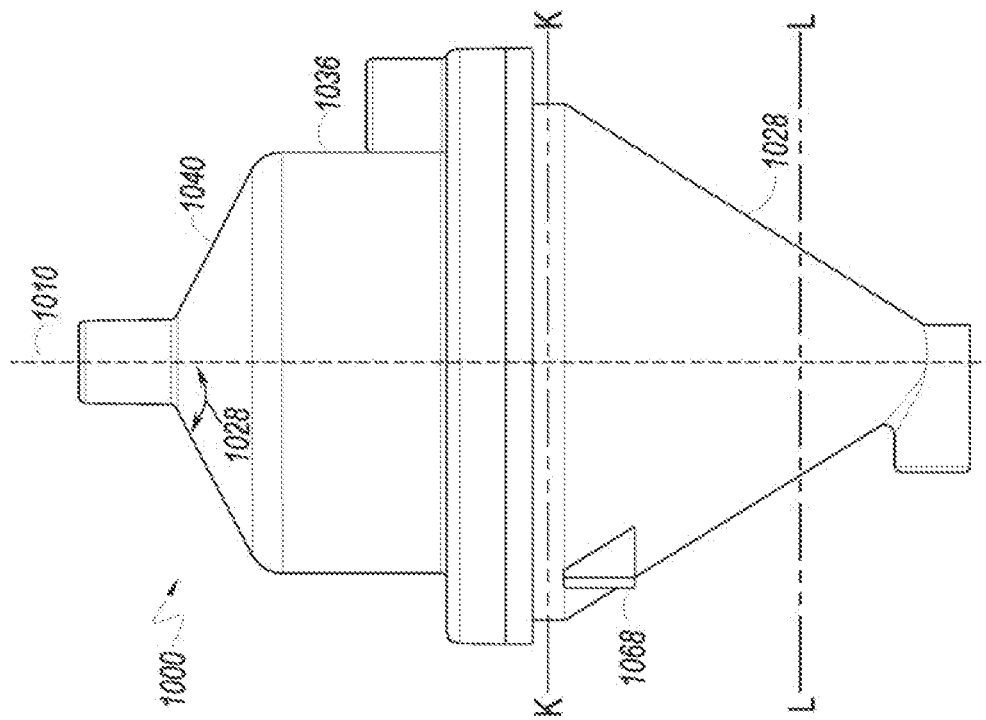
Figure 10B:
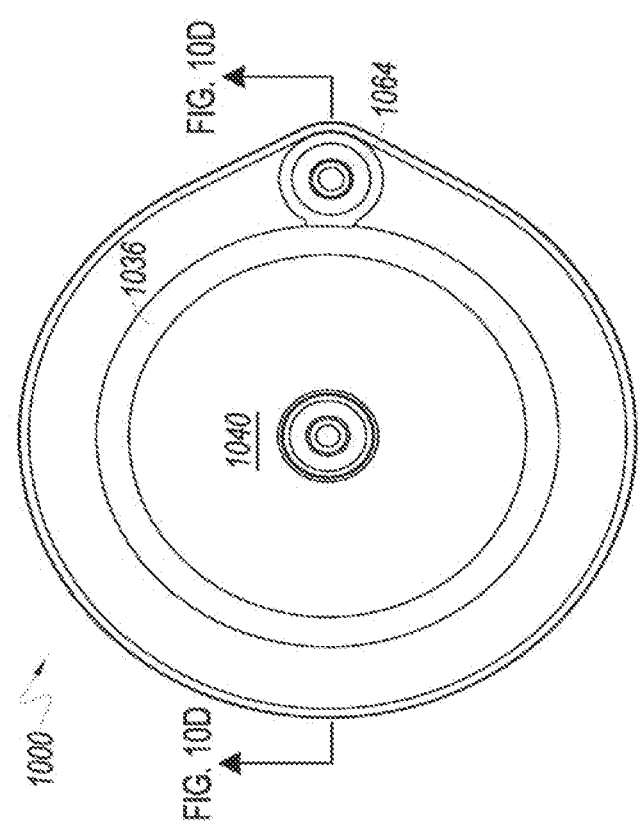

FIG. 10A illustrates a perspective view of chamber 1000; FIG. 10B illustrates a top plan view of chamber 1000; FIG. 10C illustrates a side elevation view of chamber 1000; FIG. 10D illustrates a cross-sectional view of chamber 1000; and FIG. 10E is a zoomed-in cross-sectional view around a port 1004. In some embodiments, chambers consistent with the present invention, e.g., chamber 1000, may be made from a single piece, e.g., a 3-D printed piece.

Figure 11A:
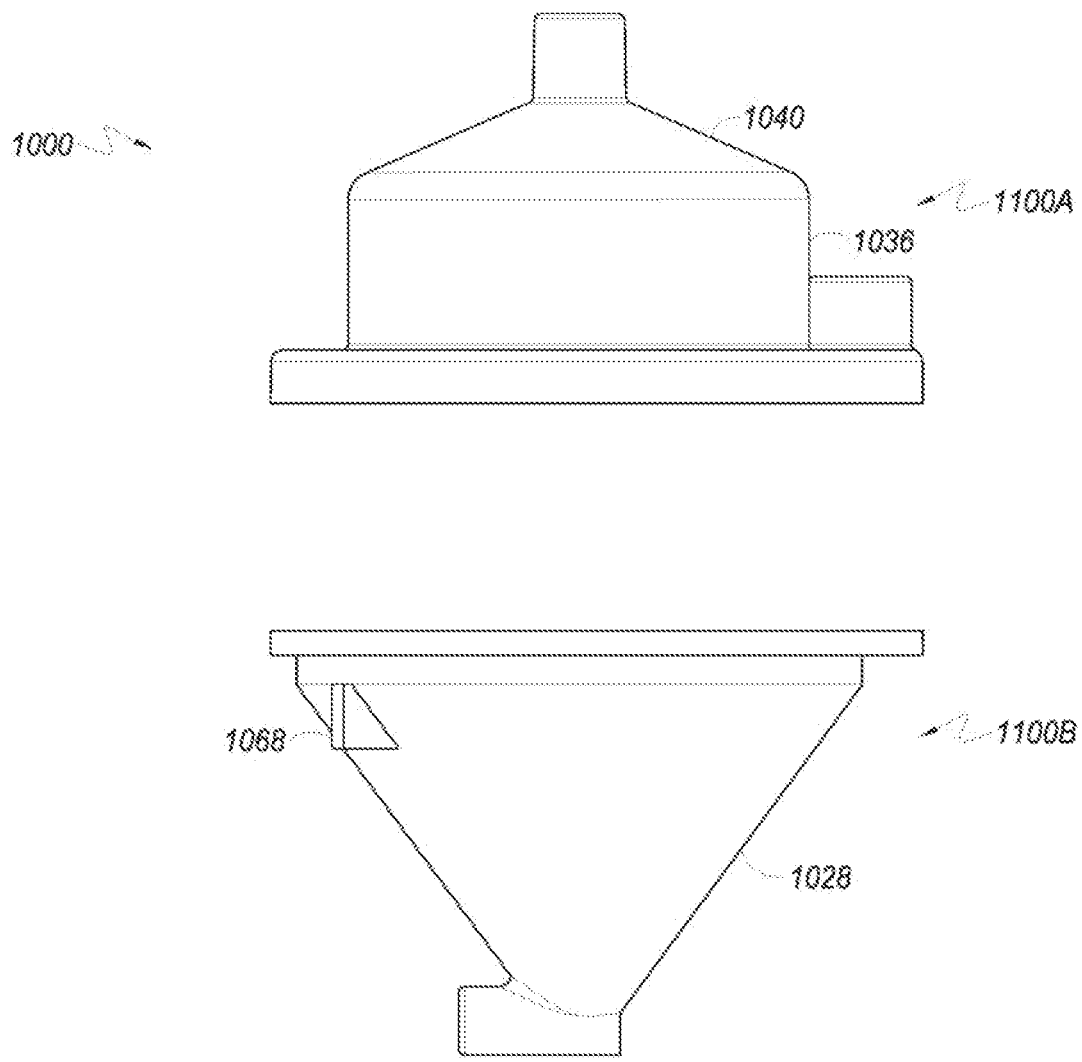
FIGS. 11A-E illustrate views of two parts of chamber 1000 according to embodiments.
Figure 11B:
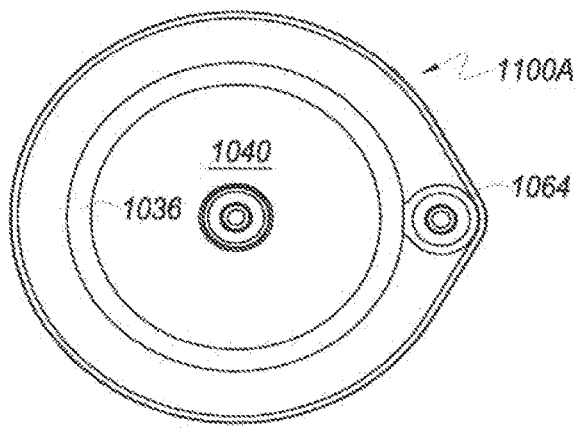
Figure 11C:
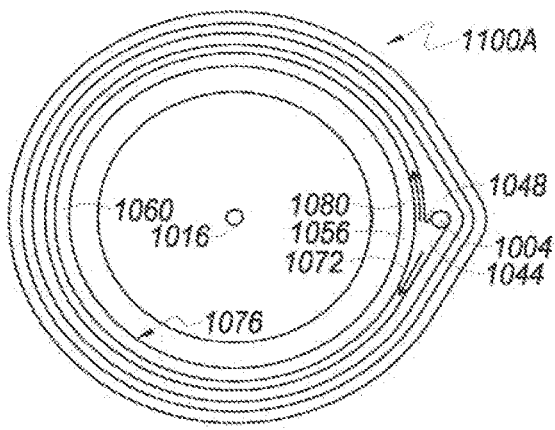
Figure 11D:
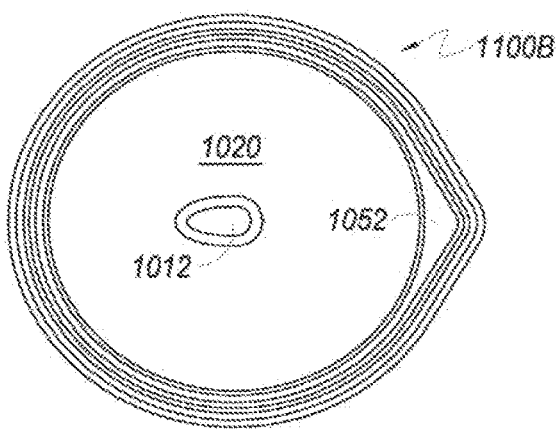
Figure 11E:
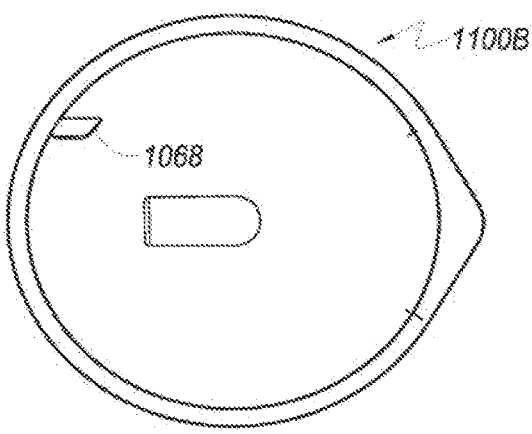

In other embodiments, chambers may be made from more than one piece FIG. 11A illustrates an exploded view of chamber 1000 showing that the chamber may be made from two pieces 1100A and 1100B. FIGS. 11B and 11C illustrate a top view and a bottom view of the first piece 1100A. FIGS. 11D and 11E illustrate a top view and a bottom view of the second piece 1100B. Reference numerals of the features described above with respect to FIGS. 10A-10E are used to refer to the same or similar features in FIGS. 11A-11E.

Referring to FIGS. 10A-E, chamber 1000 includes, inter alia, three ports. As shown in FIG. 10D, chamber 1000 includes port 1004, which is an entry port that allows liquid and particles to be introduced into a volume 1008 and may be located near a first cross section of volume 1008 (e.g., cross section of chamber through line KK in FIG. 10C). Port 1012 is an exit port through which particles and some liquid are removed from volume 1008 and may be located in a lower portion of volume 1008. Port 1012 may in embodiments also be used as an entry port to introduce a liquid into the volume 1008, such as to wash particles in volume 1008. In addition, port 1016 is an exit port through which liquid separated from the particles (in order to concentrate the particles in a smaller volume of liquid, wash the particles with the liquid, and/or treat the particles with the liquid) is removed. Port 1016 may be located in a top portion of chamber 1000.

Chamber 1000 also includes a sloped surface 1020 that directs at least a portion of particles in volume 1008 toward exit port 1012. Sloped surface 1020 slopes toward exit port 1012. In operation, chamber 1000 may be subjected to a force, e.g., gravity or centrifugal force that generally moves particles toward exit port 1012. Sloped surface 1020 aids in directing particles toward exit port 1012.

One additional feature on chamber 1000 is alignment aid 1068 on side wall 1028 (FIG. 10C). In embodiments, chamber 1000 may be positioned on a centrifuge and alignment aid 1068 may be used to ensure that when mounted on the centrifuge, chamber 1000 is in a specific orientation.

Chamber 1000 also includes side wall 1028. Side wall 1028 defines volume 1008. Side wall 1028 is angled with respect to central axis 1010 defining volume 1008 as generally conical in shape, with a circular cross section such as cross sections at line KK or LL (FIG. 10C).

Chamber 1000 also includes a second volume 1032 which is located above volume 1008. As illustrated in FIG. 10D, second volume 1032 is defined by a side wall 1036 and a top wall 1040. As shown in FIG. 10D, exit port 1016 is located in top wall 1040.

In some embodiments, the addition of a second volume may improve the processing of particles. For example, in one embodiment of processing cells, the additional volume provided by second volume 1032 allows a larger number (e.g., volume) of cells to be processed in chamber 1000. The additional volume may also be useful in embodiments where the cells may be washed, so that the wash liquid, which may be introduced through port 1012 has room to flow through the cell bed in the lower portion of volume 1008 and any cells carried into volume 1032 have time to settle back into volume 1008 instead of immediately exiting through port 1016.

Top wall 1040, which defines the second volume 1032, may in some embodiments be substantially perpendicular to central axis 1010, e.g., horizontal. Although as illustrated in FIGS. 10A-E, top wall 1040 is angled toward exit port 1016. Without being bound by theory, it is believed that in some embodiments, angling top wall 1040 toward exit port 1016 may provide a funneling effect toward exit port 1016.

In some embodiments, the angle between top wall 1040 and central axis 1010 (see angle 1088 in FIG. 10C) may be between about 90 degrees (e.g., top wall is horizontal) to about 5 degrees (e.g., top wall is steeply angled toward port 1016). In other embodiments, the angle between top wall 1040 and central axis 1010 may be between about 90 degrees and about 10 degrees, such as between about 80 degrees and about 15 degrees, or even between about 75 degrees and about 20 degrees.

Although port 1016 is shown in a particular location, e.g., collinear with the central axis 1010, in other embodiments, exit port 1016 may be located along any portion of top wall 1040. In other embodiments, exit port 1016 may be in side wall 1036. In some embodiments, the location of exit port 1016 is not limited to any specific location, except that it is located above exit port 1012.

Entry port 1004 is in sidewall 1028 and is shown in a particular location. However, in other embodiments, entry port 1004 may be located in another location in side walls 1028 or 1036. In other embodiments, entry port 1004 may be in a down tube that may extend from side wall 1028, side wall 1036, or top wall 1040. In some embodiments, the location of entry port 1004 is not limited to any specific location, except that it is located above exit port 1012.

Sloped surface 1020 is provided by side wall 1028 and slopes toward exit port 1012. Additionally, a portion of exit port 1012 is inside wall 1028. However, in other embodiments, exit port 1012 may be located in another location in side wall 1028. In some embodiments, the location of exit port 1012 is not limited to any specific location, except that it is located below entry port 1004.

FIG. 10E illustrates a zoomed-in cross-sectional view of the area near port 1004. This area includes a number of features that may be used in some embodiments. For example, a downward projecting baffle, namely wall 1056, is positioned adjacent port 1004. In embodiments, when particles in liquid are introduced through port 1004, wall 1056 directs flow of the particles in liquid toward an inside surface (e.g., surface 1020) of side wall 1028. In some embodiments, wall 1056 may be curved or angled to further direct flow toward the inside surface of side wall 1028.

In addition, chamber 1000 may also include a second downward projecting baffle, namely wall 1060 (FIG. 10D). As shown in FIG. 10D at least a portion of wall 1060 is located diametrically opposite wall 1056. In embodiments, wall 1060 may prevent flow of particles in liquid into volume 1032. For example, particles and liquid introduced through port 1004 may create a flow (e.g., a jet) that causes particles already in volume 1008 to flow into volume 1032. Wall 1060 at least partially prevents this from occurring. In some embodiments, wall 1056 and 1060 may be part of a continuous circular skirt 1076 (see FIG. 11C).

Referring again to FIG. 10E, a channel 1044 is provided that is in fluid communication with the first port 1004. The channel 1044 may be at least partially defined by wall 1056. In embodiments, the channel 1044 directs flow of particles and liquid away from first port 1004.

In embodiments, the channel 1044 may direct flow of particles away from first port 1004 in more than one direction. For example, the channel 1044 may direct flow around wall 1056 in two directions. In embodiments, a partial wall 1048 may be positioned to only allow flow of particles and liquid in one direction, e.g., in FIG. 10E out from the drawing sheet. FIG. 11C provides a different view of these features, namely channel 1044, partial wall 1048, and wall 1056 and additional description is provided below.

In some embodiments, first port 1004 may be in fluid communication with an entry pathway 1064 (FIGS. 10D and 10E) that may direct flow of particles and liquid to first port 1004. As may be appreciated, the entry pathway may direct flow from any direction to first port 1004. In one embodiment, the entry pathway may direct flow from a direction generally parallel to central axis 1010 to port 1004 (see, e.g., FIGS. 10D and 10E). In embodiments, port 1004 may include a sloped surface 1052 to direct flow from the entry pathway toward wall 1056 and/or channel 1044.

As noted above, some embodiments of chambers may be made from more than one piece, and may be attached together to form a chamber. FIG. 11A illustrates an exploded view of chamber 1000 showing that the chamber may be made from two pieces 1100A and 1100B. In embodiments, each of pieces 1100A and 1100B may be manufactured separately, e.g., molded, milled, printed, etc. and attached together using any suitable process, e.g., adhered, welded, connected by fasteners, etc. Reference numerals of the features described above with respect to FIGS. 10A-10E are used to refer to the same or similar features in FIGS. 11A-11E.

FIGS. 11B and 11C illustrate a top view and a bottom view, respectively, of the first piece 1100A. FIG. 11B provides a similar view as the plan view illustrated in FIG. 10B, showing top wall 1040, side wall 1036, and entry pathway 1064. FIG. 11C (bottom view of piece 1100A) illustrates a different view of channel 1044, partial wall 1048, wall 1056, and wall 1066 than shown in FIG. 10E.

As illustrated in FIG. 11C, wall 1056 acts as a downward projecting baffle and is adjacent to port 1004. In the embodiment illustrated in FIG. 11C, the wall 1056 is part of a skirt 1076 which extends in a circular shape and also provides wall 1060, a second downwardly projecting baffle, which is located diametrically opposite wall 1056. In other embodiments, walls 1056 and 1060 may be separate features and not be part of the continuous skirt 1076.

As shown in FIG. 11C, partial wall 1048 directs flow of particles and liquid that flow through port 1004 into channel 1044. Wall 1056, and skirt 1076, at least partially define channel 1044, which directs flow of liquid in the direction indicated by arrow 1072. In embodiments, channel 1044 directs flow of particles and liquid in a direction tangential to a sloped surface of a side wall (e.g., sloped surface 1020 provided by side wall 1028). It is noted that although channel 1044 is illustrated as directing flow in one direction, in other embodiments, partial wall 1048 may be eliminated and flow of particles and liquid may be allowed to proceed in more than one direction, e.g., at least in the direction illustrated by arrow 1072 and in the direction illustrated by arrow 1080. FIG. 11C also illustrates exit port 1016.

FIGS. 11D and 11E illustrate a top view and a bottom view, respectively, of the second piece 1100B. FIG. 11D illustrates the sloped surface 1020 provided by wall 1028, which slopes toward exit port 1012. Additionally, piece 1100B includes sloped surface 1052, which may be part of port 1004. As discussed above with respect to FIG. 10E, some embodiments provide for an entry pathway (e.g., 1064) to direct fluid to port 1004. When fluid is being directed by an entry pathway from a direction substantially parallel to central axis 1010 (FIGS. 10C and 10D) a sloped surface such as sloped surface 1052 may be used to redirect the flow toward wall 1056 and into channel 1044.

As previously described, the embodiments illustrated in FIGS. 5A-11E are provided merely for illustrative purposes. Embodiments are not necessarily limited to the structural features shown in FIGS. 5A-11E and described above. Other embodiments may include some features of the illustrated chambers and not others.

Some embodiments may include features consistent with features of some chambers shown in FIGS. 5A-11E but may not necessarily be described above. For example, some embodiments may provide chambers that include a volume with at least two cross-sectional areas; a second cross-sectional area being smaller than a first cross-sectional area. This embodiment may include some of the chambers illustrated in FIGS. 5A-11E. In other embodiments, the chamber may further provide for having an entry port next to the first cross-sectional area and an exit port (e.g., for particles) next to the second cross-sectional area, which are features of chambers 500, 600, 700, 900 and 1000. This is merely one example, and different embodiments may include other features that may not be necessarily described above but still be within the scope of the present invention.

Figure 13:
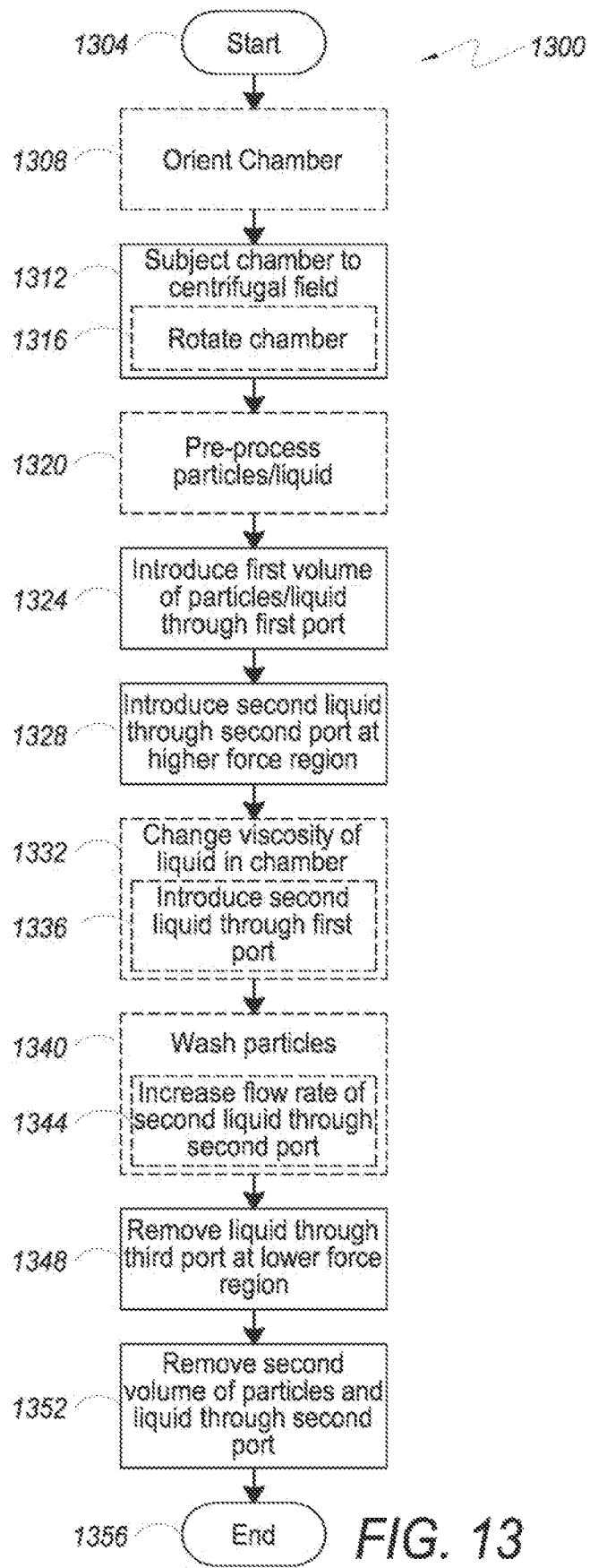
FIG. 13 illustrates a flow chart illustrating the steps of processing particles consistent with embodiment(s).
Figure 14:
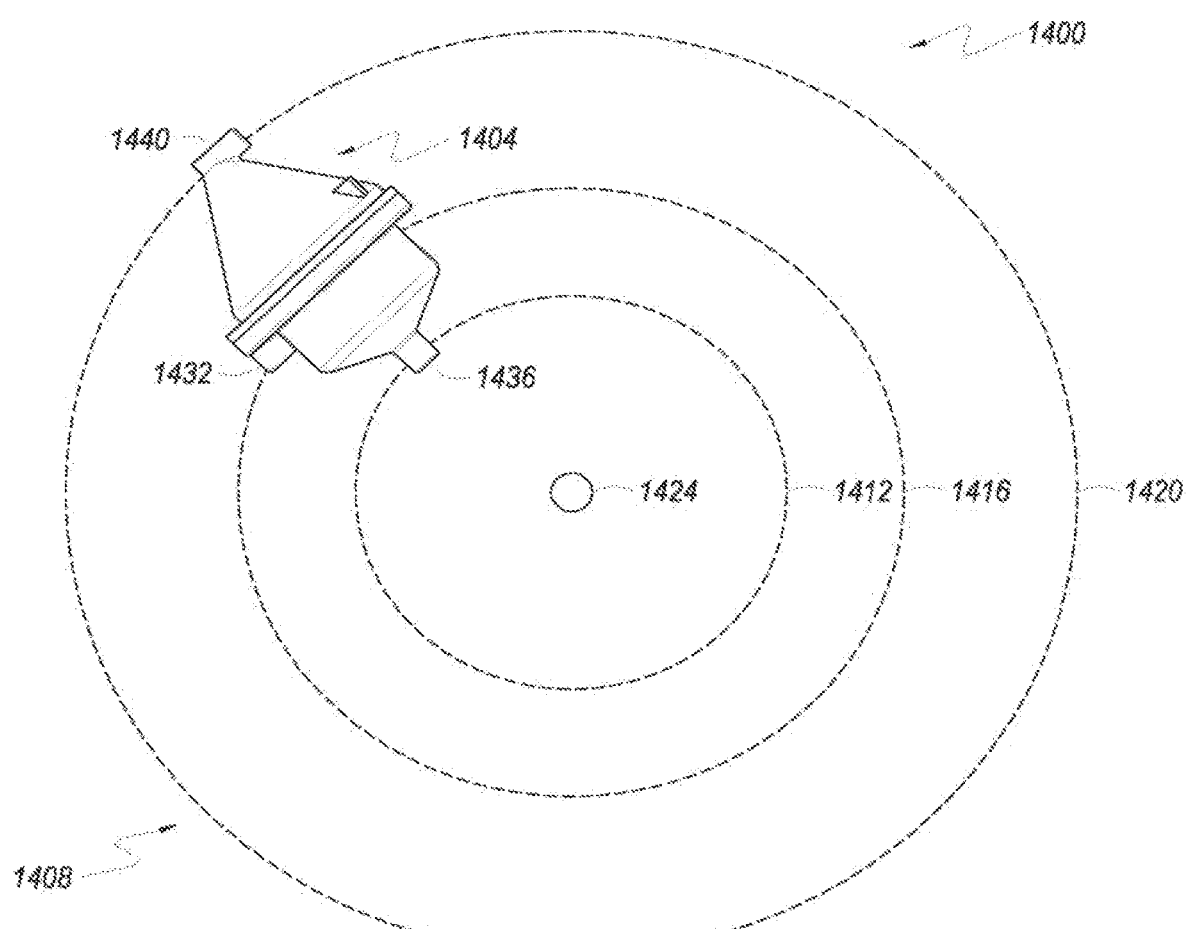
FIG. 14 illustrates a centrifugal field and chamber ports, with respect to the centrifugal field, consistent with an embodiment.

In addition to systems, tubing circuits, and chambers, some embodiments relate to methods of processing particles, such as cells, to concentrate, wash, and/or treat particles. FIGS. 12-14 describe features of some methods consistent with embodiments. It is noted that although some features of systems, tubing circuits, and chambers, may be mentioned in the description below, they are provided merely for illustrative purposes and the methods are not necessarily limited to being performed by particular chambers, systems, or tubing circuits or other structural features, but rather may be performed by the structures described above or in other embodiments by other structures.

FIG. 12 illustrates a system 1200 that includes a centrifuge 1204. The centrifuge 1204 is configured to hold chamber 1208, which as described in detail below may be used in processing particles in a liquid. Centrifuge 1204 rotates about an axis of rotation 1224. When centrifuge 1204 holds chamber 1208, the chamber is rotated. As illustrated by arrows 1240 and 1244, embodiments provide for centrifuge 1204 to rotate clockwise (arrow 1240) or counterclockwise (arrow 1244).

Chamber 1208 may have any suitable design, some of which are described above in FIGS. 5A-11E. In the embodiment shown in FIG. 12, chamber 1208 includes three ports, port 1212, port 1216, and port 1220. Port 1212 may in embodiments be an inlet for introducing particles and liquid into a volume of chamber 1208, with ports 1216 and 1220 being outlets. Although reference numerals 1212, 1216, and 1220 point to walls of chamber 1208, it is noted that the ports are perforations or holes in the wall where liquid or particles enter or leave the volume of chamber 1208. In the embodiments shown in FIG. 12, ports 1216 and 1220 are aligned with central axis 1222.

In some embodiments, methods provide for the position of one or more ports 1212, 1216, and/or 1220 during operation to be determined based on the rotation of chamber 1208 when mounted and rotating on centrifuge 1204, as is described in greater detail below.

Figure 12B:
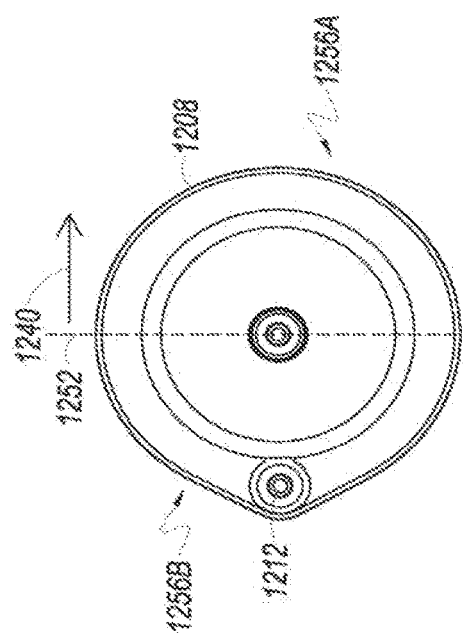
FIGS. 12A-C illustrate views of a chamber with respect to a spinning centrifuge according to embodiments.
Figure 12C:
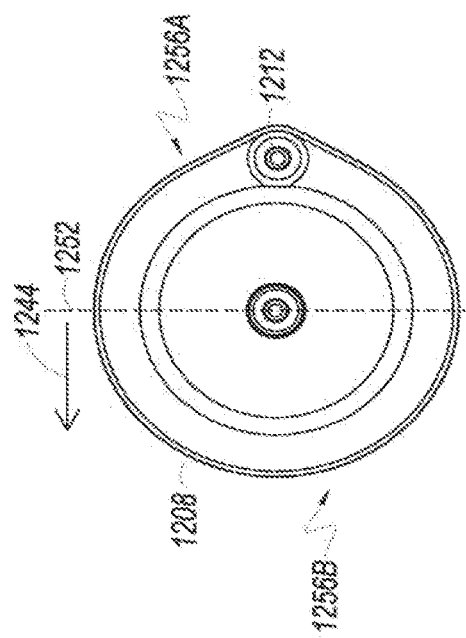
Figure 12A:
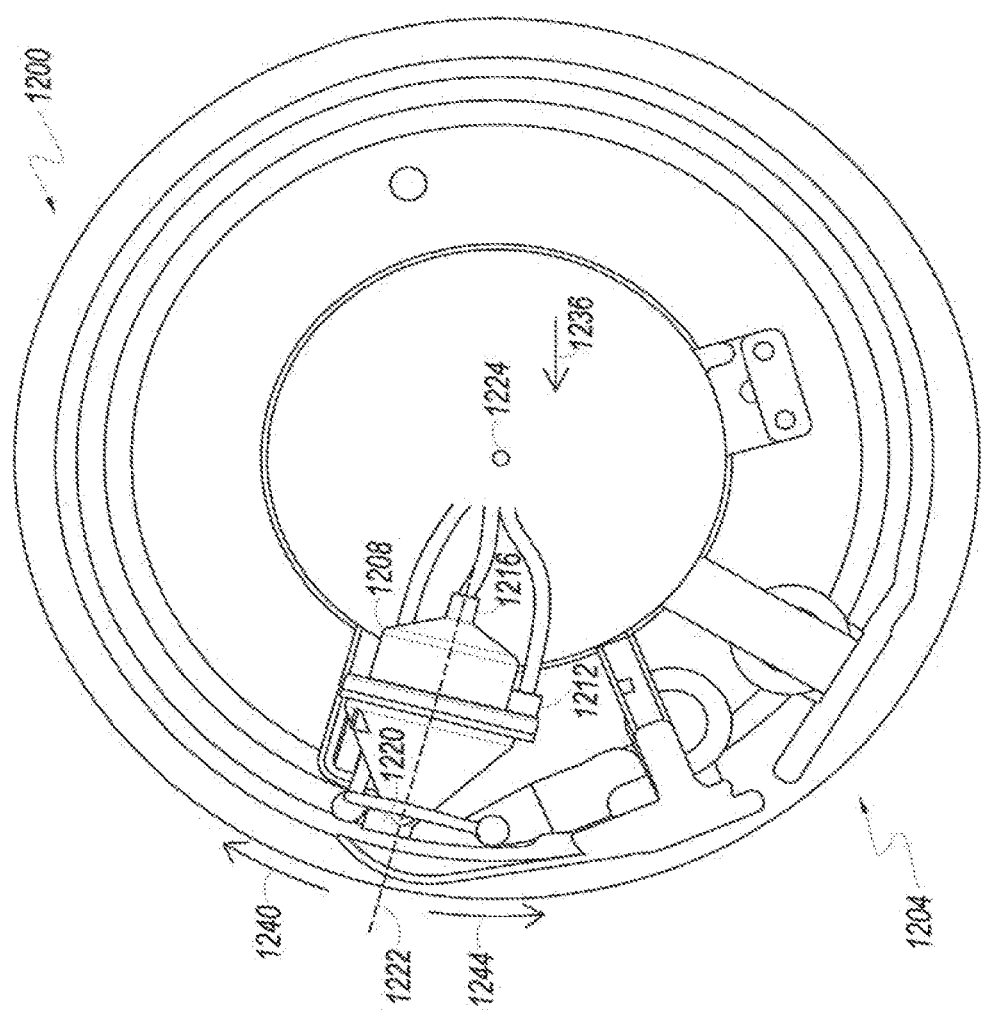

FIG. 12B illustrates a view of chamber 1208, generally from the direction illustrated by arrow 1236 (FIG. 12A). As shown in FIG. 12B, chamber 1208 is rotating clockwise as illustrated by arrow 1240. Also shown in FIG. 12B is plane 1252, which bisects chamber 1208 into a first volume 1256A and a second volume 1256B.

Similarly, FIG. 12C also illustrates a view of chamber 1208, generally from the direction illustrated by arrow 1236 (FIG. 12A). FIG. 12C shows chamber 1208 rotating counterclockwise as illustrated by arrow 1244. Also shown in FIG. 12C is plane 1252, which bisects chamber 1208 into a first volume 1256A and a second volume 1256B.

Some embodiments provide for entry port 1212 to be in a particular location depending on the rotation of chamber 1208. In some embodiments, entry port 1212 may be located in a portion of a wall of chamber 1208 that defines a trailing or leading volume, which is explained below.

In FIG. 12B, chamber 1208 is rotating clockwise, which makes the trailing volume of chamber 1208 the second portion 1256B, and the first portion 1256A is the leading volume. In embodiments where port 1212 may be located on a portion of the wall defining a trailing volume, port 1212 may be in a portion of the wall that defines volume 1256B, as shown in FIG. 12B.

In contrast, when chamber 1208 is rotating counterclockwise, such as in FIG. 12C, first volume 1256A is the trailing volume and second volume 1256B is the leading volume. In embodiments where port 1212 may be located on a portion of the wall defining a trailing volume, port 1212 may be in a portion of the wall that defines volume 1256A, as shown in FIG. 12C.

It is noted that positioning port 1212 on a portion of the wall that defines the trailing or leading volume may be done using a variety of methods. In one embodiment, when chamber 1208 is being mounted, it may be mounted in a position to ensure that entry port 1212 is in a portion of the wall defining the trailing or leading volume, whichever may be desired. The position of port 1212 may be changed merely by rotating chamber 1208 when mounting chamber 1208 on centrifuge 1204.

In other embodiments, chamber 1208 may be manufactured specifically for being rotated in a predetermined direction, e.g., clockwise or counterclockwise. In these embodiments, chamber 1208 may be manufactured with the port 1212 positioned in the appropriate portion of the wall of chamber 1208, that defines a trailing or leading volume, when chamber 1208 is mounted on centrifuge 1204 and rotated.

It should be noted that although port 1212 is illustrated in a particular location along the wall defining the trailing volume, it is not limited to the locations shown in FIGS. 12B and 12C. That is, port 1212 may be along any portion of the wall defining the trailing volume. For example, in FIG. 12B, port 1212 may be in any portion of the wall defining the trailing volume from a 6 o'clock position to a 12 o'clock position, e.g., 7 o'clock, 8 o'clock, 9 o'clock, 10 o'clock etc. Similarly, in FIG. 12C, port 1212 may be in any portion of the wall defining the trailing volume from a 12 o'clock position to a 6 o'clock position, e.g., 1 o'clock, 2 o'clock, 3 o'clock, 4 o'clock etc.

FIG. 13 illustrates a flow chart 1300 which may be performed in embodiments of the present invention. Although specific components may be described below for performing steps in flow chart 1300, the present invention is not limited thereto. For example, some steps may be described as performed by portions of system 1200, which as noted above may be implemented using system, chambers, tubing circuits, shown in FIGS. 1-11E. This is done merely for illustrative purposes, because flow chart 1300 is not limited to being performed by any specific components, structures, systems, apparatuses, chambers, or combinations thereof.

Flow 1300 begins at step 1304. Flow 1300 then passes to optional step 1308, where a chamber may be oriented. As described above, embodiments provide for chambers (that may include three ports) for processing a stream of particles and liquid, e.g., cells in a liquid medium. In embodiments, the chambers may be mounted on different separation systems that may include a centrifuge. In embodiments, optional step 1308 may be performed as part of mounting of a chamber on a separation system (e.g., 100), for example a centrifuge of a separation system. In other embodiments, the chamber may be part of a disposable tubing circuit. Optional step 1308 may be performed as part of mounting the disposable tubing circuit onto a separation system, e.g., a centrifuge of a separation system.

At step 1312, the chamber may be subjected to a centrifugal field. In some embodiments, step 1312 may include one or more optional sub-steps that are performed as part of step 1312. For example, in some embodiments, a centrifugal field may be created by rotating the chamber at sub-step 1316. In embodiments, the rotation may be performed by parts of a separation or collection system, e.g., a centrifuge.

Referring to FIG. 14, an environment 1400 is illustrated that includes a chamber 1404 being subjected to a centrifugal field 1408. In embodiments, the centrifugal field 1408 may be generated by rotating chamber 1404 around axis of rotation 1424. As illustrated by the size of circles 1412, 1416, and 1420, higher gravitational forces act on an object (e.g., chamber 1404 or particles in chamber 1404) as they get further away from the axis of rotation 1424. As illustrated in FIG. 14, chamber 1404 also includes three ports 1432, 1436, and 1440. In embodiments, chamber 1404 may have any suitable design, some of which are described above in FIGS. 5A-11E.

After step 1312, flow 1300 may pass to optional step 1320 where particles in liquid may be pre-processed. The pre-processing step may be used to initially prepare a stream or volume of particles in liquid to be processed by a chamber, such as chamber 1404.

In one embodiment, a first volume of particles in liquid may be pre-processed to reduce a volume in which the particles are carried before the volume is processed in a chamber. For example, in some embodiments, a chamber may be connected to a liquid processing vessel (see liquid processing vessel 404 in FIG. 4). In embodiments, the pre-processing may involve introducing a first volume of particles and liquid into the liquid processing vessel and removing some liquid to reduce the volume.

In other embodiments, the pre-processing may involve introducing other material into a volume of particles and liquid. The other materials may be, for example, modifiers for the particles, liquid, or other substance in the chamber volume. For example, embodiments may involve pre-processing a volume of particles and liquid by adding substances that change a viscosity, density, and/or temperature of the volume. In other embodiments, the other material may be added to modify the particles, e.g., protect or change the particles before they undergo additional processing. The foregoing are merely some examples of pre-processing steps that may be performed in some embodiments.

Flow 1300 passes to step 1324 where a first volume of particles and liquid are introduced into a volume of a chamber through a first port. It is noted that in embodiments, step 1324 provides for introducing particles and liquid through a first port, which has a specific location. For example, in one embodiment, step 1324 may involve introducing the particles and liquid through a first port in a side wall that defines a trailing volume of the chamber volume. Referring back to FIGS. 12A-12C, in these embodiments, as part of step 1324, a first port, e.g., entry port 1212 may be located in walls that define volumes 1256A or 1256B, depending on the direction of rotation.

In another embodiment, the location of the first port may be in relation to the other ports and the centrifugal field to which the chamber is subjected. For example, step 1324 may involve introducing the particles and liquid through a first port located in a higher force region than a second port, but the first port may be in a lower force region than a third port, e.g., port 1436 (FIG. 14).

At step 1328, a second liquid may be introduced into a chamber volume through a second port, which in embodiments is located in a part of the chamber being subjected to higher forces from the centrifugal field. Referring to FIG. 14, step 1324 may involve adding the volume of particles in liquid through port 1432. Step 1328 may involve adding liquid through port 1440, which as shown in FIG. 14, is located in a higher force region than port 1432.

In embodiments, the flow of the second liquid into the chamber may provide a specific function. For example, in embodiments, as the volume of particles and liquid is introduced into the chamber volume, the particles may begin to settle toward a higher force region see circle 1420 (FIG. 14). In embodiments, step 1328 may be performed to prevent the particles from packing and or agglomerating to a point that they cannot be separated or are permanently damaged. The introduction of the second liquid may also maintain the particles at least partially in a suspension.

In other embodiments, the second liquid may be added to treat the particles. For example, the second liquid may include some functional group that may change the surface chemistry of the particles. In another embodiment, the second liquid may be designed to remove functional groups to change the surface chemistry. In yet other embodiments, the second liquid may provide some predetermined environment for the particles.

It is noted that depending on the particles, the centrifugal field, the volume of the chamber, and other factors, the flow rate of the second liquid through the second port may vary. For example, in embodiments where the particles may be cells, the flow rate may be between about 1 ml/min to about 50 ml/min, such as about 2 ml/min to about 45 ml/min, about 3 ml/min to about 40 ml/min, about 4 ml/min to about 35 ml/min, or even about 5 ml/min to about 30 ml/min. In other embodiments, the flow rate of second liquid through second port may be less than about 35 ml/min, less than about 30 ml/min, less than about 25 ml/min, less than about 20 ml/min, less than about 15 ml/min, less than about 10 ml/min or even less than about 5 ml/min. In other embodiments, the flow rate of second liquid through second port may be greater than about 2 ml/min, greater than about 4 ml/min, greater than about 6 ml/min, greater than about 8 ml/min, greater than about 10 ml/min, greater than about 12 ml/min or even greater than about 14 ml/min.

After step 1328 flow 1300 passes to optional step 1332 where the viscosity of the liquid and/or particles in the chamber may be modified. Optional step 1332 may be performed in some embodiments as part of processing the particles after they have been introduced into the chamber. For example, in some embodiments, the particles may be washed or treated in the chamber. Optional step 1332 may be performed as part of the process of washing and/or treating the particles after the volume of particles to be processed have been introduced into the chamber.

In some embodiments, optional step 1332 may involve one or more sub-steps. For example, sub-step 1336 may be performed to add second liquid through the first port. Referring to FIG. 14, sub-step 1336 may involve adding the second liquid through port 1432. In some embodiments, after the viscosity has been changed at step 1332, the flow of liquid through the first port may be reduced to a rate lower than the rate initially used to change the viscosity.

In other embodiments, the viscosity change performed by step 1332 may be effected by a temperature change. The temperature change may occur in combination with addition of a liquid, e.g., sub-step 1336. For example, the second liquid introduced through the first port at sub-step 1336 may be at a predetermined temperature that allows the temperature of the particles and liquid in the chamber to be controlled. In other embodiments, step 1332 may simply involve the control of the temperature of the liquid and particles in the chamber, such as through conduction, convection, or radiation. In yet other embodiments, the second liquid may simply displace liquid already in the volume and thus change the viscosity.

Flow 1300 passes to optional step 1340 where particles in the chamber may be washed. Optional step 1340 may be performed to replace the liquid that entered the chamber with the particles, with a different liquid. Referring to FIG. 14, step 1340 may involve increasing the flow of second liquid through port 1440.

In other embodiments, optional step 1340 may be performed to, in addition to replacing liquid, also remove a material from the particles or the liquid. For example, in embodiments where the particles may be cells, the cells may initially be in a liquid medium that includes a variety of proteins, nutrients, and waste materials. Optional step 1340 may be used to remove these materials from the cells before the cells may be used for research or therapeutic purposes.

Optional step 1340 may in embodiments involve one or more sub-steps. For example, in embodiments, sub-step 1344 may be performed to increase the flow rate of the second liquid through the second port. In embodiments, the additional flow rate of liquid will flow through the particles that have previously been maintained in suspension by the flow rate of liquid through the second port.

Depending on the particles, the centrifugal field, the volume of the chamber, and other factors, the increase of flow rate of the second liquid through the second port may vary. For example, in embodiments where the particles may be cells, the flow rate of the second liquid through the second port may be increased to between about 5 ml/min to about 100 ml/min, such as about 10 ml/min to about 90 ml/min, about 15 ml/min to about 85 ml/min, about 20 ml/min to about 80 ml/min, or even about 25 ml/min to about 75 ml/min. In other embodiments, the flow rate of second liquid through second port may be less than about 70 ml/min, less than about 65 ml/min, less than about 60 ml/min, less than about 55 ml/min, less than about 50 ml/min, less than about 45 ml/min or even less than about 40 ml/min. In other embodiments, the flow rate of second liquid through second port may be greater than about 5 ml/min, greater than about 10 ml/min, greater than about 15 ml/min, greater than about 20 ml/min, greater than about 25 ml/min, greater than about 30 ml/min or even greater than about 35 ml/min.

In some embodiments, step 1340 may also be performed to treat the particles. The second liquid may include some material that may be used to modify the particles, or surround them with some predetermined environment.

Flow 1300 then passes to step 1348 where liquid is removed through a third port at a lower force region. Referring to FIG. 14, step 1348 may involve removing liquid through port 1436. It is noted that step 1348 may be performed continuously throughout various steps of flow 1300. For example, as particles and liquid are introduced into the chamber at step 1324, liquid may begin to be removed from the chamber through the third port. Also, as flow rates of liquid are increased, e.g., steps 1336, 1344, liquid may be removed through the third port.

Flow 1300 passes from step 1348 to step 1352 where a second volume of particles and liquid are removed through the second port. Referring to FIG. 14, the second volume of particles and liquid may be removed through port 1440. Flow 1300 then ends at step 1356.

As noted above, flow 1300 may be utilized in processing any combination of particles and liquid to concentrate, wash, and or treat particles. In several embodiments, flow 1300 may be used to concentrate and wash cells that may be grown for research or therapeutic purposes. For example, in embodiments, a cell containing liquid may be generated from cells that are grown in a liquid media. The cell containing liquid may be from a cell expansion system. One example of a cell expansion system is described in U.S. Pat. Nos. 8,309,347; and 8,785,181, which are hereby incorporated by reference in their entirety as if set forth herein in full. It is noted that the cells may be any type of cells, some non-limiting examples including T-cells, mesenchymal stem cells, fibroblasts, red blood cells, leukocytes, etc.

In some embodiments, a volume of cells and liquid may be processed using some or all of the steps of flow 1300, in combination with chamber 1000 (FIG. 10A-E). In embodiments, steps 1312, 1316, 1324, 1328, 1348, and 1352 of flow 1300 may be performed.

Chamber 1000 may be rotated to subject the chamber to the centrifugal field (e.g., steps 1312 and 1316). A volume of cells, e.g., T-cells, may be introduced into the volume 1008 through port 1004 (e.g., step 1324). After the first volume of cells and liquid is introduced, a second liquid may be introduced through port 1012 (e.g., step 1328) to maintain the particles in suspension.

The centrifugal field may push cells toward exit port 1012. The cells may be concentrated because the liquid introduced into the chamber volume 1008 with the particles may flow out of the chamber through port 1016 (e.g., step 1348). Step 1328 may ensure that as the particles are being concentrated, they do not pack or permanently agglomerate. Finally, at step 1352, a second volume of cells and liquid that is less than the first volume may be removed.

In other embodiments, not only are the cells concentrated, but they may be additionally processed by being washed. In these embodiments, optional steps 1332, 1336, 1340, and 1344 may be performed in addition to steps 1312, 1316, 1324, 1328, 1348, and 1352.

Accordingly, after the first volume of cells and liquid is introduced into chamber 1000, and second liquid is flowing into the chamber through port 1012, (steps 1324 and 1328), step 1332 may be performed to change a viscosity of the liquid in volume 1008. This step may be performed by adding a second liquid, e.g., a wash liquid into volume 1008 through, for example, port 1004 (e.g., step 1336).

Step 1340 may be performed by adding the second liquid (e.g., increasing the flow rate) into port 1012. The second liquid may flow through the bed of cells and out of the chamber through the port 1016. As noted above, step 1332 is performed to change the viscosity of the liquid in the chamber to allow the wash liquid introduced at step 1340 to displace the liquid in the chamber and wash the liquid and any other materials in the liquid out through the port 1016. The concentrated and washed cells may then be removed through the port 1012 at step 1352.

In some embodiments, a large range of volumes of cells and liquid (e.g., first volume) may be processed using the steps of flow 1300. The volumes may range from several hundred milliliters up to a hundred liters. In some embodiments, flow 1300 may process (wash and concentrate) volumes of about 10 liters in about 60 minutes or less, such as a volume of about 5 liters in about 30 minutes or less, or a volume of about 3 liters in about 20 minutes or less.

In some embodiments, flow 1300 (e.g., in combination with chamber 1000) may be performed to accomplish volume reductions of about 50%, about 60%, about 70%, about 80%, about 90%, or even about 95%. Also, depending on the conditions and other parameters, the cell loss, e.g., the difference between the number of cells in the original volume and the number of cells in the final volume, may be less than about 10%, less than about 5%, less than about 4%, less than about 3%, less than about 2%, less than about 1%, or even less than about 0.5%. That is, the volume of cells in the second volume may include greater than about 85% of the cells in the first volume, greater than about 90% of the cells in the first volume, greater than about 95% of the cells in the first volume, greater than about 98% of the cells in the first volume, greater than about 99% of the cells in the first volume, greater than about 99.5% of the cells in the first volume, or even 99.9% of the cells in the first volume.

It is noted that although the description above has been made with respect to a batch process, where a volume of particles and liquid are processed (e.g., concentrated, washed, and/or treated), flow 1300 and the chambers 500, 600, 700, 800, 900, and 1000, described above, may also be used in processes that are continuous.

As may be appreciated, in some embodiments, a volume of particles may exceed the capacity of a chamber. In these embodiments, step 1352 may be performed periodically in order to remove particles from the chamber. With step 1352 being performed periodically, a continuous process of concentrating particles may be performed. Removing the particles from the chamber may be performed using a number of techniques. For example, a pump may be used to pump particles out of the chamber volume.

In other embodiments, a continuous process may be implemented by modifying a ratio of flow rate through two ports. Using chamber 1000 as an example, a ratio of the flow rate of liquid and particles through port 1004 and a flow rate of liquid trough port 1012 may be used. In other words, the flow rate though port 1012 may be reduced (or the flow rate through port 1004 may be increased) so that particles are pushed through port 1012 and into a pathway (e.g., tubing) in fluid communication with port 1012. In embodiments, a container or other storage volume may be connected in fluid communication with port 1012 to provide additional volume for storing particles in a continuous process.

It will be apparent to those skilled in the art that various modifications and variations can be made to the methods and structure of the present invention without departing from its scope. Thus it should be understood that the invention is not be limited to the specific embodiments or examples given.

Rather, the invention is intended to cover modifications and variations within the scope of the following claims and their equivalents.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A particle separation chamber comprising:
   a housing having an interior space, the housing having a sidewall with a first cross-sectional area at a first end and a second cross-sectional area at a second end, the second cross-sectional area being greater than the first cross-sectional area, the sidewall including two pairs of opposing sidewalls that together define the interior space, and a first pair of the two pairs of opposing sidewalls includes a first opposing sidewall having a first length and a second opposing sidewall having a second length that is different from the first length;
   a first port configured to introduce a first volume of fluid into the interior space;
   a second port configured to remove a second volume of fluid from the interior space; and
   a third port configured to remove a third volume of fluid from the interior space,
   wherein a location of the second port is provided closer to the first end of the housing than a location of the first port, and a location of the third port is provided closer to the second end of the housing than the location of the second port.

2. The particle separation chamber of claim 1, wherein the first volume of fluid includes a first volume of liquid and particles.

3. The particle separation chamber of claim 1, wherein the second volume of fluid includes a second volume of liquid and particles.

4. The particle separation chamber of claim 1, wherein the third volume of fluid includes a third volume of liquid only.

5. The particle separation chamber of claim 1, wherein the second port is configured to introduce a fourth volume of fluid into the internal space.

6. The chamber of claim 1, wherein the first cross-sectional area is of a rectangular cross-section.

7. The chamber of claim 6, wherein the second cross-sectional area is of a rectangular cross-section.

8. The chamber of claim 1, wherein the housing includes a top wall.

9. The chamber of claim 8, wherein the first port is arranged in the sidewall.

10. The chamber of claim 8, wherein the first port is arranged in the top wall.

11. The chamber of claim 8, wherein the third port is arranged in the top wall.

12. A particle processing method comprising:
   rotating a chamber to generate a centrifugal field, the chamber including a housing having an interior space subjected to the centrifugal field, the housing including a sidewall with a first cross-sectional area at a first end and a second cross-sectional area at a second end, the second cross-sectional area being greater than the first cross-sectional area, the sidewall including two pairs of opposing sidewalls that together define the interior space, and a first pair of the two pairs of opposing sidewalls includes a first opposing sidewall having a first length and a second opposing sidewall having a second length that is different from the first length;

introducing a first volume of fluid into the interior space through a first port in the housing;

removing a second volume of fluid from the interior space through a second port in the housing, a location of the second port being provided closer to the first end of the housing than a location of the first port; and removing a third volume of fluid from the interior space through a third port in the housing, a location of the third port being provided closer to the second end of the housing than the location of the second port.

13. The method of claim 12, further comprising:

after the introducing the first volume of fluid and before removing the second volume of fluid, changing the viscosity of fluid in the interior space of the housing.

14. The method of claim 12, wherein the first volume of fluid includes a first volume of liquid and particles.

15. The method of claim 12, wherein the second volume of fluid is less than the first volume of fluid.

16. The method of claim 12, wherein the second volume of fluid includes a second volume of liquid and particles.

17. The method of claim 12, wherein the third volume of fluid includes a third volume of liquid only.

18. The method of claim 12, further comprising:

after introducing the first volume of fluid into the interior space, introducing a fourth volume of fluid into the interior space through the second port in the housing.

* * * * *